(12) United States Patent
Kool

(10) Patent No.: US 7,482,332 B2
(45) Date of Patent: Jan. 27, 2009

(54) TELOMERE-ENCODING SYNTHETIC DNA NANOCIRCLES, AND THEIR USE FOR THE ELONGATION OF TELOMERE REPEATS

(75) Inventor: Eric T Kool, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 904 days.

(21) Appl. No.: 10/336,265

(22) Filed: Jan. 3, 2003

(65) Prior Publication Data

US 2003/0148988 A1 Aug. 7, 2003

Related U.S. Application Data

(60) Provisional application No. 60/345,056, filed on Jan. 4, 2002.

(51) Int. Cl.
*A61K 48/00* (2006.01)
*C12N 15/11* (2006.01)

(52) U.S. Cl. .......................... 514/44; 536/23.1
(58) Field of Classification Search ............... 536/24.1, 536/24.2, 24.33, 23.1; 514/44
See application file for complete search history.

(56) References Cited

U.S. PATENT DOCUMENTS

| | | | |
|---|---|---|---|
| 5,683,874 A | 11/1997 | Kool | 435/6 |
| 5,714,320 A | 2/1998 | Kool | 435/6 |
| 5,872,105 A | 2/1999 | Kool | 514/44 |
| 6,077,668 A | 6/2000 | Kool | 435/6 |
| 6,096,880 A | 8/2000 | Kool | 536/25.3 |

OTHER PUBLICATIONS

Hanish et al. (Proc. Natl. Acad. Sci, U.S.A., vol. 91, pp. 8861-8865; 1994).*
Wellinger, RJ et al. European Journal of Cancer, vol. 33 No. 5 pp. 735-749, 1997.*
Daubendiek, S.L. et al. J. Amer. Chem. Soc. 1995, vol. 117, pp. 7818-7819.*
T.M. Nakamura et al., "Telomerase Catalytic Subunit Homologs from Fission Yeast and Human," *Science* vol. 277, pp. 955-959, 1997.
Meyersen, M. et al., "hEST2, the Putative Human Telomerase Catalytic Subunit Gene, is Up-Regulated in Tumor Cells and during Immortalization," *Cell* vol. 90 pp. 785-795, 1997.
Weinrich, S.L. et al., "Reconstitution of human telomerase with the template RNA component hTR and the catalytic protein subunit hTRT," *Nature Genetics*, vol. 17(4), pp. 498-502, 1997.
Regev A. et al., "Telomeric repeats on small polydisperse circular DNA (spcDNA) and genomic instability," *Oncogene*, vol. 17, pp. 3455-3461, 1998.
Cech, T.R., "Life at the End of the Chromosome: Telomeres and Telomerase," *Angewandte Chemie Int. Ed.*, vol. 39(1), pp. 34-43, 2000.
Fire, A. et al., "Rolling replication of short DNA circles," *Proc. Natl. Acad. Sci. U.S.A.*, vol. 92(10), pp. 4641-4645, 1995.

Liu, D. et al., "Rolling Circle DNA Synthesis: Small Circular Oligonucleotides as Efficient Templates for DNA Polymerases," *J. Am. Chem. Soc.* 1996, 118, pp. 1587-1594.
Nakai, H., "Amplification of Bacteriophafe Mu DNA by Rolling Circle DNA Replication in Vitro," *The Journal of Biological Chemistry*, vol. 268, pp. 23997-24004, 1993.
Daubendiek, S.L. et al., "Generation of Catalytic RNAs by Rolling Transcription of Synthetic DNA Nanocircles," *Nature Biotechnology*, vol. 15(3), pp. 273-277, 1997.
Diegelman, A. et al., "Generation of Circular RNAs and *trans*-cleaving catalytic RNAs by rolling transcription of circular DNA oligonycleotides encoding hairpin ribozymes," *Nucleic Acids Research*, vol. 26(13), pp. 3235-3241, 1998.
Andras, S.C., et al., "Strategies for Signal Amplification in Nucleic Acid Detection," *Molecular Biotechnology*, vol. 19(1), 29-44, 2001.
Christian, A.T. et al. "Detection of DNA point mutations and mRNA expression levels by rolling circle amplification in individual cells," *Proc.Natl. Acad. Sci.*, USA, vol. 98(25), pp. 14238-14243, 2001.
Funk, W.D., et al., "Telomerase Expression Restores Dermal Integrity to in Vitro-Aged Fibroblasts in a Reconstituted Skin Model," *Experimental Cell Research*, vol. 258(2), pp. 270-278, 2000.
Lee, J.J., "Telomere length changes in patients undergoing hematopietic stem cell transplantation," *Bone Marrow Transplantation*, vol. 24(4), pp. 411-415, 1999.
Hahn, W.C., "Creation of Human Tumour Cells with Defined Genetic Elements," *Nature*, 400, pp. 464-468, 1999.
Kim, M.M. et al., "A low threshold level of expression of mutant-template telomerase RNA inhibits human tumor cell proliferation," *Proc. Natl. Acad. Sciences USA*, vol. 98(14), pp. 7982-7987, 2001.
Chen, J. et al., "G-quadruplex as a new class of structural entities for directing the formation of circular oligodeoxyribonucleotides," *ChemComm*, vol. 22, pp. 2686-2687, 2002.
Li, T. et al., "Construction of Circular Oligodeoxyribonucleotides on the New Structural Basis of I-Motif," *Journal of the American Chemical Society*, vol. 123(51), pp. 12901-12902, 2001.
Natarahan, S. et al., "Recombinational Telomere Elongation Promoted by DNA Circles," *Molecular and Cellular Briology* vol. 22(13), pp. 4512-4521, 2002.

(Continued)

*Primary Examiner*—J. E Angell
(74) *Attorney, Agent, or Firm*—Howrey LLP

(57) ABSTRACT

Telomere-encoding nucleic acid nanocircles, methods for their preparation, and methods for their use are disclosed. The nanocircles can be constructed containing multiple repeats of the complement of telomere repeat sequences. The telomere-encoding nanocircles are useful for extending telomeres both in vitro and in vivo, for treating macular degeneration, the effects of skin aging, liver degeneration, and cancer. The nanocircles are further useful for treating cell cultures to produce long-lived non-cancerous cell populations. This use has wide applicability in scientific research, tissue engineering, and transplantation.

7 Claims, 11 Drawing Sheets

OTHER PUBLICATIONS

Engelhardt, M., et al. "Telomerase Regulation, Cell Cycle, and Telomere Stability in Primitive Hematopoietic Cells" *Blood, Journ. Amer. Soc. Hemat.*, vol. 90(1), pp. 182-193, 1997.

Daubendiek, S.L., et al., "Rolling-Circle RNA Synthesis: Circular Oligonucleotides as Efficient Substrates for T7 RNA Polymerase," *Journal of the American Chemical Society*, vol. 117(29), pp. 7818-7819, 1995.

Lindstrom, U.M., et al. "An orthogonal oligonucleotide protecting group strategy that enables assembly of repetitive or highly structured DNAs," *Nucleic Acid Research*, vol. 30(19), e101, 2002.

Yaswen, P., et al. "Epigenetic Changes Accompanying Human Mammary Epithelial Cell Immortalization," *Journal of Mammary Gland Biology and Neoplasia*, vol. 6(2), pp. 223-234, 2001.

Bodnar, A.G., et al. "Extension of Life-Span by Introduction of Telomerase into Normal Human Cells," *Science Magazine*, 279, pp. 349-352, 1999.

McEachem, M.J., et al. "Telomeres and their Control," *Annual Review Genetics*, 34, pp. 331-358, 2000.

T.L. Halvorsen et al., "Accelerated telomere shortening and senescence in human pancreatic islet cells stimulated to divide in vitro;" *Journal of Endocrinology* (2000) 166, 103-109; online version www.endocrinology.org.

Lindstrom, U. et al. Artificil human telomeres from DNA nanocircle templates. Proceedings of the Natl. Acad. Sci, U.S.A., Dec. 10, 2002, vol. 99, No. 24, pp. 15953-15958.

International Search Report from PCT/US03/00109, dated Oct. 31, 2003.

* cited by examiner

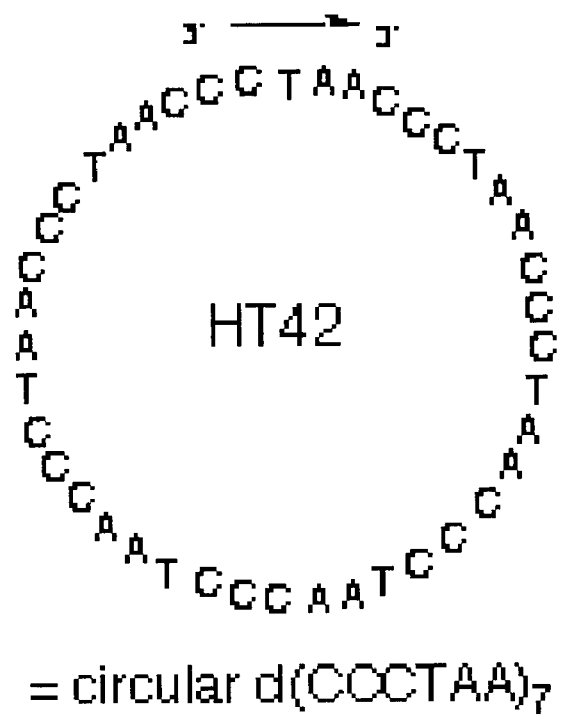
= circular d(CCCTAA)₇
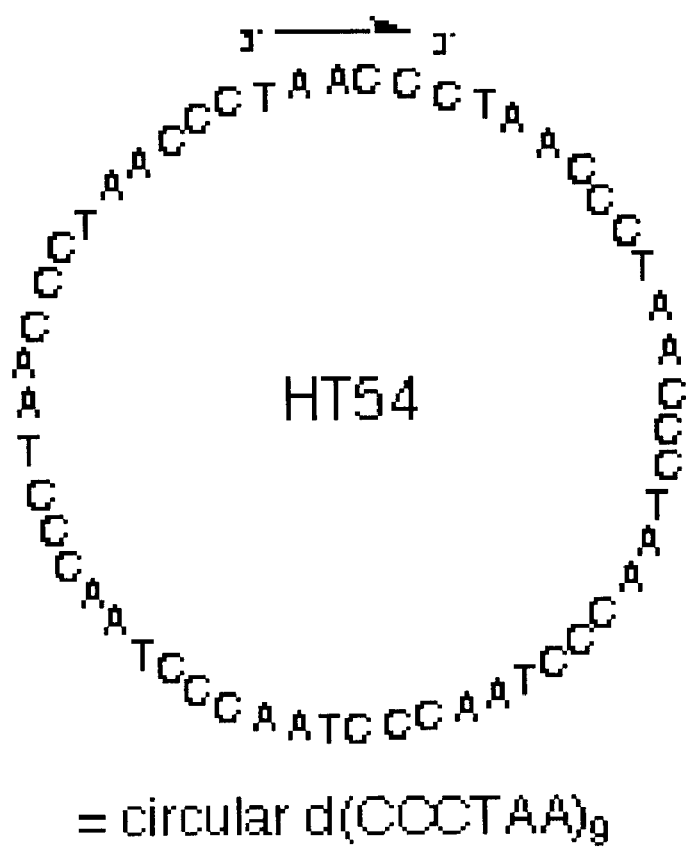
= circular d(CCCTAA)₉

= circular d(CCCTAA)₁₂

= circular d(CCCTAA)₉(CCCACA)₂ scrambled version of YT54:

circular
5'-dCAC TCC ACT CCA CAC CTC
   ACC AAA CTC CAC AAC CAC
   AAC ACC ACA CTC ACT CCT-3' circular
5'-dCAC TCC ACT CAC AAC ATC
   CAC ACC TCA CAC TAC AAC
   TCC AAC ACA CTC ACT CCT-3'

N4-Ac-deoxycytidine-5'DMT-
3'cyanoethylphosphoramidite

N6-PAC-deoxyadenosine-5'DMT-
3'cyanoethylphosphoramidite

N2-4-ipr-PAC-deoxyguanosine-5'DMT-
3'cyanoethylphosphoramidite

N6-dma-deoxyadenosine-5'DMT-
3'cyanoethylphosphoramidite

SEQUENCE LISTING

```
<160> NUMBER OF SEQ ID NOS: 64

<210> SEQ ID NO 1
<211> LENGTH: 6
<212> TYPE: DNA
<213> ORGANISM: Homo sapiens

<400> SEQUENCE: 1 ttaggg                                                                     6

<210> SEQ ID NO 2
<211> LENGTH: 6
<212> TYPE: DNA
<213> ORGANISM: Saccharomyces cerevisiae

<400> SEQUENCE: 2 tgtggg                                                                     6

<210> SEQ ID NO 3
<211> LENGTH: 6
<212> TYPE: DNA
<213> ORGANISM: Homo sapiens

<400> SEQUENCE: 3 ccctaa                                                                     6

<210> SEQ ID NO 4
<211> LENGTH: 6
<212> TYPE: RNA
<213> ORGANISM: Homo sapiens

<400> SEQUENCE: 4 cccuaa                                                                     6

<210> SEQ ID NO 5
<211> LENGTH: 6
<212> TYPE: DNA
```

<213> ORGANISM: Saccharomyces cerevisiae

<400> SEQUENCE: 5 cccaca                                                                 6

<210> SEQ ID NO 6
<211> LENGTH: 20
<212> TYPE: DNA
<213> ORGANISM: Homo sapiens

<400> SEQUENCE: 6
agggtgtggg tgtgggttag                                                 20

<210> SEQ ID NO 7
<211> LENGTH: 5
<212> TYPE: DNA
<213> ORGANISM: Homo sapiens

<400> SEQUENCE: 7 cagat                                                                  5

<210> SEQ ID NO 8
<211> LENGTH: 5
<212> TYPE: DNA
<213> ORGANISM: Artificial sequence
<220> FEATURE:
<223> OTHER INFORMATION: Synthetic: Sequence used to assay deprotection
      methods
<220> FEATURE:
<221> NAME/KEY: misc_feature
<222> LOCATION: (4)..(4)
<223> OTHER INFORMATION: dmaA

<400> SEQUENCE: 8 cagnt                                                                  5

<210> SEQ ID NO 9
<211> LENGTH: 5
<212> TYPE: DNA
<213> ORGANISM: Artificial sequence
<220> FEATURE:
<223> OTHER INFORMATION: Synthetic: Sequence used to assay deprotection
      methods
<220> FEATURE:
<221> NAME/KEY: misc_feature
<222> LOCATION: (1)..(1)
<223> OTHER INFORMATION: N = ac4c
<220> FEATURE:
<221> NAME/KEY: misc_feature
<222> LOCATION: (2)..(2)
<223> OTHER INFORMATION: N = pacA
<220> FEATURE:
<221> NAME/KEY: misc_feature
<222> LOCATION: (3)..(3)
<223> OTHER INFORMATION: N = ipr-pacG
<220> FEATURE:
<221> NAME/KEY: misc_feature
<222> LOCATION: (4)..(4)
<223> OTHER INFORMATION: N = dmaA

<400> SEQUENCE: 9 nnnnt                                                                  5

<210> SEQ ID NO 10
<211> LENGTH: 5
<212> TYPE: DNA
<213> ORGANISM: Artificial sequence
<220> FEATURE:
<223> OTHER INFORMATION: Synthetic: Sequence used to assay deprotection

```
                methods
<220> FEATURE:
<221> NAME/KEY: misc_feature
<222> LOCATION: (4)..(4)
<223> OTHER INFORMATION: N = dmaA

<400> SEQUENCE: 10 cagnt                                                                      5

<210> SEQ ID NO 11
<211> LENGTH: 18
<212> TYPE: DNA
<213> ORGANISM: Homo sapiens

<400> SEQUENCE: 11
ttagggttag ggttaggg                                                       18

<210> SEQ ID NO 12
<211> LENGTH: 42
<212> TYPE: DNA
<213> ORGANISM: Artificial sequence
<220> FEATURE:
<223> OTHER INFORMATION: Synthetic: protected nanocircle precursor
<220> FEATURE:
<221> NAME/KEY: misc_feature
<222> LOCATION: (1)..(2)
<223> OTHER INFORMATION: N = pacA
<220> FEATURE:
<221> NAME/KEY: misc_feature
<222> LOCATION: (3)..(5)
<223> OTHER INFORMATION: N = ac4c
<220> FEATURE:
<221> NAME/KEY: misc_feature
<222> LOCATION: (7)..(8)
<223> OTHER INFORMATION: N = pacA
<220> FEATURE:
<221> NAME/KEY: misc_feature
<222> LOCATION: (9)..(11)
<223> OTHER INFORMATION: N = ac4c
<220> FEATURE:
<221> NAME/KEY: misc_feature
<222> LOCATION: (13)..(14)
<223> OTHER INFORMATION: N = dmaA
<220> FEATURE:
<221> NAME/KEY: misc_feature
<222> LOCATION: (15)..(17)
<223> OTHER INFORMATION: N = ac4c
<220> FEATURE:
<221> NAME/KEY: misc_feature
<222> LOCATION: (19)..(20)
<223> OTHER INFORMATION: N = dmaA
<220> FEATURE:
<221> NAME/KEY: misc_feature
<222> LOCATION: (21)..(23)
<223> OTHER INFORMATION: N = ac4c
<220> FEATURE:
<221> NAME/KEY: misc_feature
<222> LOCATION: (25)..(26)
<223> OTHER INFORMATION: N = dmaA
<220> FEATURE:
<221> NAME/KEY: misc_feature
<222> LOCATION: (27)..(29)
<223> OTHER INFORMATION: N = ac4c
<220> FEATURE:
<221> NAME/KEY: misc_feature
<222> LOCATION: (31)..(32)
<223> OTHER INFORMATION: N = dmaA
<220> FEATURE:
<221> NAME/KEY: misc_feature
<222> LOCATION: (33)..(35)
<223> OTHER INFORMATION: N = ac4c
<220> FEATURE:
<221> NAME/KEY: misc_feature
<222> LOCATION: (37)..(38)
<223> OTHER INFORMATION: N = pacA
```

```
<220> FEATURE:
<221> NAME/KEY: misc_feature
<222> LOCATION: (39)..(41)
<223> OTHER INFORMATION: N = ac4c

<400> SEQUENCE: 12
nnnnntnnnn ntnnnnntnn nnntnnnnnt nnnnntnnnn nt                    42

<210> SEQ ID NO 13
<211> LENGTH: 20
<212> TYPE: DNA
<213> ORGANISM: Homo sapiens

<400> SEQUENCE: 13
ggttagggtt agggttaggg                                             20

<210> SEQ ID NO 14
<211> LENGTH: 54
<212> TYPE: DNA
<213> ORGANISM: Artificial sequence
<220> FEATURE:
<223> OTHER INFORMATION: Synthetic: protected nanocircle precursor
<220> FEATURE:
<221> NAME/KEY: misc_feature
<222> LOCATION: (1)..(2)
<223> OTHER INFORMATION: N = pacA
<220> FEATURE:
<221> NAME/KEY: misc_feature
<222> LOCATION: (3)..(5)
<223> OTHER INFORMATION: N = ac4c
<220> FEATURE:
<221> NAME/KEY: misc_feature
<222> LOCATION: (7)..(8)
<223> OTHER INFORMATION: N = pacA
<220> FEATURE:
<221> NAME/KEY: misc_feature
<222> LOCATION: (9)..(11)
<223> OTHER INFORMATION: N = ac4c
<220> FEATURE:
<221> NAME/KEY: misc_feature
<222> LOCATION: (13)..(14)
<223> OTHER INFORMATION: N = dmaA
<220> FEATURE:
<221> NAME/KEY: misc_feature
<222> LOCATION: (15)..(17)
<223> OTHER INFORMATION: N = ac4c
<220> FEATURE:
<221> NAME/KEY: misc_feature
<222> LOCATION: (19)..(20)
<223> OTHER INFORMATION: N = dmaA
<220> FEATURE:
<221> NAME/KEY: misc_feature
<222> LOCATION: (21)..(23)
<223> OTHER INFORMATION: N = ac4c
<220> FEATURE:
<221> NAME/KEY: misc_feature
<222> LOCATION: (25)..(26)
<223> OTHER INFORMATION: N = dmaA
<220> FEATURE:
<221> NAME/KEY: misc_feature
<222> LOCATION: (27)..(29)
<223> OTHER INFORMATION: N = ac4c
<220> FEATURE:
<221> NAME/KEY: misc_feature
<222> LOCATION: (31)..(32)
<223> OTHER INFORMATION: N = dmaA
<220> FEATURE:
<221> NAME/KEY: misc_feature
<222> LOCATION: (33)..(35)
<223> OTHER INFORMATION: N = ac4c
<220> FEATURE:
<221> NAME/KEY: misc_feature
<222> LOCATION: (37)..(38)
<223> OTHER INFORMATION: N = dmaA
<220> FEATURE:
```

<221> NAME/KEY: misc_feature
<222> LOCATION: (39)..(41)
<223> OTHER INFORMATION: N = ac4c
<220> FEATURE:
<221> NAME/KEY: misc_feature
<222> LOCATION: (43)..(44)
<223> OTHER INFORMATION: N = dmaA
<220> FEATURE:
<221> NAME/KEY: misc_feature
<222> LOCATION: (45)..(47)
<223> OTHER INFORMATION: N = ac4c
<220> FEATURE:
<221> NAME/KEY: misc_feature
<222> LOCATION: (49)..(50)
<223> OTHER INFORMATION: N = pacA
<220> FEATURE:
<221> NAME/KEY: misc_feature
<222> LOCATION: (51)..(53)
<223> OTHER INFORMATION: N = ac4c

<400> SEQUENCE: 14
nnnnntnnnn ntnnnnntnn nnntnnnnnt nnnnntnnnn ntnnnnntnn nnnt        54

<210> SEQ ID NO 15
<211> LENGTH: 18
<212> TYPE: DNA
<213> ORGANISM: Homo sapiens

<400> SEQUENCE: 15
gttagggtta gggttagg                                                 18

<210> SEQ ID NO 16
<211> LENGTH: 72
<212> TYPE: DNA
<213> ORGANISM: Artificial sequence
<220> FEATURE:
<223> OTHER INFORMATION: Synthetic: protected nanocircle precursor
<220> FEATURE:
<221> NAME/KEY: misc_feature
<222> LOCATION: (1)..(2)
<223> OTHER INFORMATION: N = pacA
<220> FEATURE:
<221> NAME/KEY: misc_feature
<222> LOCATION: (3)..(5)
<223> OTHER INFORMATION: N = ac4c
<220> FEATURE:
<221> NAME/KEY: misc_feature
<222> LOCATION: (7)..(8)
<223> OTHER INFORMATION: N = pacA
<220> FEATURE:
<221> NAME/KEY: misc_feature
<222> LOCATION: (9)..(11)
<223> OTHER INFORMATION: N = ac4c
<220> FEATURE:
<221> NAME/KEY: misc_feature
<222> LOCATION: (13)..(14)
<223> OTHER INFORMATION: N = dmaA
<220> FEATURE:
<221> NAME/KEY: misc_feature
<222> LOCATION: (15)..(17)
<223> OTHER INFORMATION: N = ac4c
<220> FEATURE:
<221> NAME/KEY: misc_feature
<222> LOCATION: (19)..(20)
<223> OTHER INFORMATION: N = dmaA
<220> FEATURE:
<221> NAME/KEY: misc_feature
<222> LOCATION: (21)..(23)
<223> OTHER INFORMATION: N = ac4c
<220> FEATURE:
<221> NAME/KEY: misc_feature
<222> LOCATION: (25)..(26)
<223> OTHER INFORMATION: N = dmaA
<220> FEATURE:
<221> NAME/KEY: misc_feature

```
<222> LOCATION: (27)..(29)
<223> OTHER INFORMATION: N = ac4c
<220> FEATURE:
<221> NAME/KEY: misc_feature
<222> LOCATION: (31)..(32)
<223> OTHER INFORMATION: N = dmaA
<220> FEATURE:
<221> NAME/KEY: misc_feature
<222> LOCATION: (33)..(35)
<223> OTHER INFORMATION: N = ac4c
<220> FEATURE:
<221> NAME/KEY: misc_feature
<222> LOCATION: (37)..(38)
<223> OTHER INFORMATION: N = dmaA
<220> FEATURE:
<221> NAME/KEY: misc_feature
<222> LOCATION: (39)..(41)
<223> OTHER INFORMATION: N = ac4c
<220> FEATURE:
<221> NAME/KEY: misc_feature
<222> LOCATION: (43)..(44)
<223> OTHER INFORMATION: N = dmaA
<220> FEATURE:
<221> NAME/KEY: misc_feature
<222> LOCATION: (45)..(47)
<223> OTHER INFORMATION: N = ac4c
<220> FEATURE:
<221> NAME/KEY: misc_feature
<222> LOCATION: (49)..(50)
<223> OTHER INFORMATION: N = dmaA
<220> FEATURE:
<221> NAME/KEY: misc_feature
<222> LOCATION: (51)..(53)
<223> OTHER INFORMATION: N = ac4c
<220> FEATURE:
<221> NAME/KEY: misc_feature
<222> LOCATION: (55)..(56)
<223> OTHER INFORMATION: N = dmaA
<220> FEATURE:
<221> NAME/KEY: misc_feature
<222> LOCATION: (57)..(59)
<223> OTHER INFORMATION: N = ac4c
<220> FEATURE:
<221> NAME/KEY: misc_feature
<222> LOCATION: (61)..(62)
<223> OTHER INFORMATION: N = dmaA
<220> FEATURE:
<221> NAME/KEY: misc_feature
<222> LOCATION: (63)..(65)
<223> OTHER INFORMATION: N = ac4c
<220> FEATURE:
<221> NAME/KEY: misc_feature
<222> LOCATION: (67)..(68)
<223> OTHER INFORMATION: N = pacA
<220> FEATURE:
<221> NAME/KEY: misc_feature
<222> LOCATION: (69)..(71)
<223> OTHER INFORMATION: N = ac4c

<400> SEQUENCE: 16
nnnnntnnnn ntnnnnntnn nnntnnnnnt nnnnntnnnn ntnnnnntnn nnntnnnnnt      60
nnnnntnnnn nt                                                          72

<210> SEQ ID NO 17
<211> LENGTH: 20
<212> TYPE: DNA
<213> ORGANISM: Homo sapiens

<400> SEQUENCE: 17
ggttagggtt agggttaggg                                                  20

<210> SEQ ID NO 18
<211> LENGTH: 54
<212> TYPE: DNA
```

<213> ORGANISM: Saccharomyces cerevisiae

<400> SEQUENCE: 18
cccacaccct aaccctaacc ctaaccctaa ccctaaccct aaccctaacc caca    54

<210> SEQ ID NO 19
<211> LENGTH: 20
<212> TYPE: DNA
<213> ORGANISM: Saccharomyces cerevisiae

<400> SEQUENCE: 19
agggtgtggg tgtgggttag    20

<210> SEQ ID NO 20
<211> LENGTH: 54
<212> TYPE: DNA
<213> ORGANISM: Saccharomyces cerevisiae

<400> SEQUENCE: 20
cactccactc cacacctcac caaactccac aaccacaaca ccacactcac tcct    54

<210> SEQ ID NO 21
<211> LENGTH: 20
<212> TYPE: DNA
<213> ORGANISM: Saccharomyces cerevisiae

<400> SEQUENCE: 21
gagtggagtg aggagtgagt    20

<210> SEQ ID NO 22
<211> LENGTH: 54
<212> TYPE: DNA
<213> ORGANISM: Homo sapiens

<400> SEQUENCE: 22
cactccactc acaacatcca cacctcacac tacaactcca acacactcac tcct    54

<210> SEQ ID NO 23
<211> LENGTH: 20
<212> TYPE: DNA
<213> ORGANISM: Homo sapiens

<400> SEQUENCE: 23
gtgtggagtg aggagtgagt    20

<210> SEQ ID NO 24
<211> LENGTH: 54
<212> TYPE: DNA
<213> ORGANISM: Artificial sequence
<220> FEATURE:
<223> OTHER INFORMATION: Synthetic: protected nanocircle precursor
<220> FEATURE:
<221> NAME/KEY: misc_feature
<222> LOCATION: (1)..(2)
<223> OTHER INFORMATION: N = pacA
<220> FEATURE:
<221> NAME/KEY: misc_feature
<222> LOCATION: (3)..(5)
<223> OTHER INFORMATION: N = acetyl-5-methyl cytidine
<220> FEATURE:
<221> NAME/KEY: misc_feature
<222> LOCATION: (7)..(8)
<223> OTHER INFORMATION: N = pacA
<220> FEATURE:
<221> NAME/KEY: misc_feature
<222> LOCATION: (9)..(11)
<223> OTHER INFORMATION: N = acetyl-5-methyl cytidine

```
<220> FEATURE:
<221> NAME/KEY: misc_feature
<222> LOCATION: (13)..(14)
<223> OTHER INFORMATION: N = dmaA
<220> FEATURE:
<221> NAME/KEY: misc_feature
<222> LOCATION: (15)..(17)
<223> OTHER INFORMATION: N = acetyl-5-methyl cytidine
<220> FEATURE:
<221> NAME/KEY: misc_feature
<222> LOCATION: (19)..(20)
<223> OTHER INFORMATION: N = dmaA
<220> FEATURE:
<221> NAME/KEY: misc_feature
<222> LOCATION: (21)..(23)
<223> OTHER INFORMATION: N = acetyl-5-methyl cytidine
<220> FEATURE:
<221> NAME/KEY: misc_feature
<222> LOCATION: (25)..(26)
<223> OTHER INFORMATION: N = dmaA
<220> FEATURE:
<221> NAME/KEY: misc_feature
<222> LOCATION: (27)..(29)
<223> OTHER INFORMATION: N = acetyl-5-methyl cytidine
<220> FEATURE:
<221> NAME/KEY: misc_feature
<222> LOCATION: (31)..(32)
<223> OTHER INFORMATION: N = dmaA
<220> FEATURE:
<221> NAME/KEY: misc_feature
<222> LOCATION: (33)..(35)
<223> OTHER INFORMATION: N = acetyl-5-methyl cytidine
<220> FEATURE:
<221> NAME/KEY: misc_feature
<222> LOCATION: (37)..(38)
<223> OTHER INFORMATION: N = dmaA
<220> FEATURE:
<221> NAME/KEY: misc_feature
<222> LOCATION: (39)..(41)
<223> OTHER INFORMATION: N = acetyl-5-methyl cytidine
<220> FEATURE:
<221> NAME/KEY: misc_feature
<222> LOCATION: (43)..(44)
<223> OTHER INFORMATION: N = dmaA
<220> FEATURE:
<221> NAME/KEY: misc_feature
<222> LOCATION: (45)..(47)
<223> OTHER INFORMATION: N = acetyl-5-methyl cytidine
<220> FEATURE:
<221> NAME/KEY: misc_feature
<222> LOCATION: (49)..(50)
<223> OTHER INFORMATION: N = pacA
<220> FEATURE:
<221> NAME/KEY: misc_feature
<222> LOCATION: (51)..(53)
<223> OTHER INFORMATION: N = acetyl-5-methyl cytidine

<400> SEQUENCE: 24
nnnnntnnnn ntnnnnntnn nnntnnnnnt nnnnntnnnn ntnnnnntnn nnnt          54

<210> SEQ ID NO 25
<211> LENGTH: 20
<212> TYPE: DNA
<213> ORGANISM: Homo sapiens

<400> SEQUENCE: 25
ggttagggtt agggttaggg                                                20

<210> SEQ ID NO 26
<211> LENGTH: 30
<212> TYPE: DNA
<213> ORGANISM: Homo sapiens

<400> SEQUENCE: 26
```

-continued

```
ccctaaccct aaccctaacc ctaaccctaa                                        30
```

<210> SEQ ID NO 27
<211> LENGTH: 36
<212> TYPE: DNA
<213> ORGANISM: Homo sapiens

<400> SEQUENCE: 27

```
ccctaaccct aaccctaacc ctaaccctaa ccctaa                                 36
```

<210> SEQ ID NO 28
<211> LENGTH: 42
<212> TYPE: DNA
<213> ORGANISM: Homo sapiens

<400> SEQUENCE: 28

```
ccctaaccct aaccctaacc ctaaccctaa ccctaaccct aa                          42
```

<210> SEQ ID NO 29
<211> LENGTH: 48
<212> TYPE: DNA
<213> ORGANISM: Homo sapiens

<400> SEQUENCE: 29

```
ccctaaccct aaccctaacc ctaaccctaa ccctaaccct aaccctaa                    48
```

<210> SEQ ID NO 30
<211> LENGTH: 54
<212> TYPE: DNA
<213> ORGANISM: Homo sapiens

<400> SEQUENCE: 30

```
ccctaaccct aaccctaacc ctaaccctaa ccctaaccct aaccctaacc ctaa             54
```

<210> SEQ ID NO 31
<211> LENGTH: 60
<212> TYPE: DNA
<213> ORGANISM: Homo sapiens

<400> SEQUENCE: 31

```
ccctaaccct aaccctaacc ctaaccctaa ccctaaccct aaccctaacc ctaaccctaa       60
```

<210> SEQ ID NO 32
<211> LENGTH: 66
<212> TYPE: DNA
<213> ORGANISM: Homo sapiens

<400> SEQUENCE: 32

```
ccctaaccct aaccctaacc ctaaccctaa ccctaaccct aaccctaacc ctaaccctaa       60
ccctaa                                                                 66
```

<210> SEQ ID NO 33
<211> LENGTH: 72
<212> TYPE: DNA
<213> ORGANISM: Homo sapiens

<400> SEQUENCE: 33

```
ccctaaccct aaccctaacc ctaaccctaa ccctaaccct aaccctaacc ctaaccctaa       60
ccctaaccct aa                                                          72
```

<210> SEQ ID NO 34
<211> LENGTH: 78

```
<212> TYPE: DNA
<213> ORGANISM: Homo sapiens

<400> SEQUENCE: 34 ccctaacccct aaccctaacc ctaaccctaa ccctaacccct aaccctaacc ctaaccctaa      60 ccctaacccct aaccctaa                                                     78

<210> SEQ ID NO 35
<211> LENGTH: 66
<212> TYPE: DNA
<213> ORGANISM: Artificial sequence
<220> FEATURE:
<223> OTHER INFORMATION: Synthetic: nanocircle containing 7 repeats of
      Seq. ID No: 3 and 2 repeats of Seq. ID No: 5

<400> SEQUENCE: 35 ccctaacccct aaccctaacc ctaaccctaa ccctaacccct aaccctaacc ctaacccaca      60
cccaca                                                                   66

<210> SEQ ID NO 36
<211> LENGTH: 54
<212> TYPE: DNA
<213> ORGANISM: Saccharomyces cerevisiae

<400> SEQUENCE: 36
cactccactc cacacctcac caaactccac aaccacaaca ccacactcac tcct              54

<210> SEQ ID NO 37
<211> LENGTH: 54
<212> TYPE: DNA
<213> ORGANISM: Homo sapiens

<400> SEQUENCE: 37
cactccactc acaacatcca cacctcacac tacaactcca acacactcac tcct              54

<210> SEQ ID NO 38
<211> LENGTH: 54
<212> TYPE: DNA
<213> ORGANISM: Homo sapiens
<220> FEATURE:
<221> NAME/KEY: misc_feature
<222> LOCATION: (1)..(3)
<223> OTHER INFORMATION: N = acetyl-5-methyl cytidine
<220> FEATURE:
<221> NAME/KEY: misc_feature
<222> LOCATION: (7)..(9)
<223> OTHER INFORMATION: N = acetyl-5-methyl cytidine
<220> FEATURE:
<221> NAME/KEY: misc_feature
<222> LOCATION: (13)..(15)
<223> OTHER INFORMATION: N = acetyl-5-methyl cytidine
<220> FEATURE:
<221> NAME/KEY: misc_feature
<222> LOCATION: (19)..(21)
<223> OTHER INFORMATION: N = acetyl-5-methyl cytidine
<220> FEATURE:
<221> NAME/KEY: misc_feature
<222> LOCATION: (25)..(27)
<223> OTHER INFORMATION: N = acetyl-5-methyl cytidine
<220> FEATURE:
<221> NAME/KEY: misc_feature
<222> LOCATION: (31)..(33)
<223> OTHER INFORMATION: N = acetyl-5-methyl cytidine
<220> FEATURE:
<221> NAME/KEY: misc_feature
<222> LOCATION: (37)..(39)
<223> OTHER INFORMATION: N = acetyl-5-methyl cytidine
<220> FEATURE:
<221> NAME/KEY: misc_feature
```

```
<222> LOCATION: (43)..(45)
<223> OTHER INFORMATION: N = acetyl-5-methyl cytidine
<220> FEATURE:
<221> NAME/KEY: misc_feature
<222> LOCATION: (49)..(51)
<223> OTHER INFORMATION: N = acetyl-5-methyl cytidine

<400> SEQUENCE: 38
nnntaannnt aannntaann ntaannntaa nnntaannnt aannntaann ntaa        54

<210> SEQ ID NO 39
<211> LENGTH: 6
<212> TYPE: DNA
<213> ORGANISM: Tetrahymena thermophila

<400> SEQUENCE: 39 ttgggg                                                              6

<210> SEQ ID NO 40
<211> LENGTH: 6
<212> TYPE: DNA
<213> ORGANISM: Paramecium aurelia
<220> FEATURE:
<221> NAME/KEY: misc_feature
<222> LOCATION: (3)..(3)
<223> OTHER INFORMATION: N = T or G

<400> SEQUENCE: 40 ttnggg                                                              6

<210> SEQ ID NO 41
<211> LENGTH: 8
<212> TYPE: DNA
<213> ORGANISM: Oxytrichia fallax

<400> SEQUENCE: 41 ttttgggg                                                            8

<210> SEQ ID NO 42
<211> LENGTH: 2
<212> TYPE: DNA
<213> ORGANISM: Dictyostelium discoideum
<220> FEATURE:
<221> NAME/KEY: misc_feature
<222> LOCATION: (2)..(2)
<223> OTHER INFORMATION: n= (G)1-8

<400> SEQUENCE: 42 an                                                                  2

<210> SEQ ID NO 43
<211> LENGTH: 5
<212> TYPE: DNA
<213> ORGANISM: Giardia ardeae

<400> SEQUENCE: 43 taggg                                                               5

<210> SEQ ID NO 44
<211> LENGTH: 7
<212> TYPE: DNA
<213> ORGANISM: Plasmodium falciparum
<220> FEATURE:
<221> NAME/KEY: misc_feature
<222> LOCATION: (3)..(3)
<223> OTHER INFORMATION: N = T or C
```

```
<400> SEQUENCE: 44 ttnaggg                                                                  7

<210> SEQ ID NO 45
<211> LENGTH: 3
<212> TYPE: DNA
<213> ORGANISM: Saccharomyces cerevisiae
<220> FEATURE:
<221> NAME/KEY: misc_feature
<222> LOCATION: (2)..(2)
<223> OTHER INFORMATION: N = (G) 2-3
<220> FEATURE:
<221> NAME/KEY: misc_feature
<222> LOCATION: (3)..(3)
<223> OTHER INFORMATION: N = (TG) 1-6

<400> SEQUENCE: 45 tnn                                                                      3

<210> SEQ ID NO 46
<211> LENGTH: 6
<212> TYPE: DNA
<213> ORGANISM: Schizosaccharomyces pombe
<220> FEATURE:
<221> NAME/KEY: misc_feature
<222> LOCATION: (6)..(6)
<223> OTHER INFORMATION: N = (G) 2-5

<400> SEQUENCE: 46 ttacan                                                                   6

<210> SEQ ID NO 47
<211> LENGTH: 23
<212> TYPE: DNA
<213> ORGANISM: Candida albicans

<400> SEQUENCE: 47
acggatgtct aacttcttgg tgt                                               23

<210> SEQ ID NO 48
<211> LENGTH: 25
<212> TYPE: DNA
<213> ORGANISM: Kluyveromyces lactis

<400> SEQUENCE: 48
acggatttga ttaggtatgt ggtgt                                             25

<210> SEQ ID NO 49
<211> LENGTH: 16
<212> TYPE: DNA
<213> ORGANISM: Candida glabrata

<400> SEQUENCE: 49
ctgggtgctg tggggt                                                       16

<210> SEQ ID NO 50
<211> LENGTH: 14
<212> TYPE: DNA
<213> ORGANISM: Candida tropicalis

<400> SEQUENCE: 50
ggggtctggg tgct                                                         14

<210> SEQ ID NO 51
<211> LENGTH: 22
```

```
<212> TYPE: DNA
<213> ORGANISM: Candida maltosa

<400> SEQUENCE: 51
ggtgtacgga tgtctaactt ct                                              22

<210> SEQ ID NO 52
<211> LENGTH: 22
<212> TYPE: DNA
<213> ORGANISM: Candida guillermondii
<220> FEATURE:
<221> NAME/KEY: misc_feature
<222> LOCATION: (7)..(7)
<223> OTHER INFORMATION: N = C or A

<400> SEQUENCE: 52
ggtgtangga tgtcacgatc at                                              22

<210> SEQ ID NO 53
<211> LENGTH: 23
<212> TYPE: DNA
<213> ORGANISM: Candida pseudotropicalis

<400> SEQUENCE: 53
ggtgtacgga tgcagactcg ctt                                             23

<210> SEQ ID NO 54
<211> LENGTH: 4
<212> TYPE: DNA
<213> ORGANISM: Cryptococcus neoformans
<220> FEATURE:
<221> NAME/KEY: misc_feature
<222> LOCATION: (4)..(4)
<223> OTHER INFORMATION: N = (G) 4-6

<400> SEQUENCE: 54 ttan                                                                   4

<210> SEQ ID NO 55
<211> LENGTH: 6
<212> TYPE: DNA
<213> ORGANISM: Ascaris lumbricoides

<400> SEQUENCE: 55 ttaggc                                                                 6

<210> SEQ ID NO 56
<211> LENGTH: 5
<212> TYPE: DNA
<213> ORGANISM: Parascaris univalens

<400> SEQUENCE: 56 ttgca                                                                  5

<210> SEQ ID NO 57
<211> LENGTH: 5
<212> TYPE: DNA
<213> ORGANISM: Bombyx mori

<400> SEQUENCE: 57 ttagg                                                                  5

<210> SEQ ID NO 58
<211> LENGTH: 8
<212> TYPE: DNA
```

```
<213> ORGANISM: Chlamydomonas reinhardtii

<400> SEQUENCE: 58 ttttaggg                                                             8

<210> SEQ ID NO 59
<211> LENGTH: 6
<212> TYPE: DNA
<213> ORGANISM: Homo sapiens
<220> FEATURE:
<221> NAME/KEY: misc_feature
<222> LOCATION: (3)..(3)
<223> OTHER INFORMATION: N = T or A

<400> SEQUENCE: 59 ttnggg                                                               6

<210> SEQ ID NO 60
<211> LENGTH: 18
<212> TYPE: DNA
<213> ORGANISM: Homo sapiens

<400> SEQUENCE: 60
ttagggttag ggttaggg                                                 18

<210> SEQ ID NO 61
<211> LENGTH: 18
<212> TYPE: DNA
<213> ORGANISM: Homo sapiens

<400> SEQUENCE: 61
ccctaaccct aaccctaa                                                 18

<210> SEQ ID NO 62
<211> LENGTH: 54
<212> TYPE: DNA
<213> ORGANISM: Homo sapiens

<400> SEQUENCE: 62
ttagggttag ggttagggtt agggttaggg ttagggttag ggttagggtt aggg         54

<210> SEQ ID NO 63
<211> LENGTH: 6
<212> TYPE: DNA
<213> ORGANISM: Homo sapiens

<400> SEQUENCE: 63 ttaggg                                                               6

<210> SEQ ID NO 64
<211> LENGTH: 6
<212> TYPE: RNA
<213> ORGANISM: Homo sapiens

<400> SEQUENCE: 64 uuaggg                                                               6
```

TELOMERE-ENCODING SYNTHETIC DNA NANOCIRCLES, AND THEIR USE FOR THE ELONGATION OF TELOMERE REPEATS

CROSS REFERENCE TO RELATED APPLICATIONS

The present application claims priority to U.S. Provisional Patent Application Ser. No. 60/345,056 filed Jan. 4, 2002, the contents of all of which are incorporated herein by reference.

STATEMENT REGARDING FEDERALLY SPONSORED RESEARCH OR DEVELOPMENT

The government may own rights in the present invention pursuant to grant number DAMD17-98-1-8239 from the U.S. Army Breast Cancer Research Program.

FIELD OF THE INVENTION

The invention relates to compositions and methods for the extension of telomere repeat sequences and, more specifically, to the use of synthetic nucleic acid nanocircles for the extension of telomere repeat sequences. The invention further relates to synthetic, diagnostic, and therapeutic uses for the nanocircles. The many potential uses of telomere-encoding nanocircles include their use to enhance the lifespan of non-cancerous cell populations in culture, to treat macular degeneration, to treat skin aging, to treat liver degeneration, and to treat cancer. Additionally, nanocircles can be used to elongate telomeres in vitro, to add synthetic telomeres onto chemicals or biomolecules having a telomere primer, and to add detectable or modified bases into a telomere.

BACKGROUND OF THE INVENTION

Human cell populations typically have a finite lifetime, dividing a number of times before entering a nondividing phase called "replicative senescence". Human chromosomes are capped with repeated sequences called "telomeres". Human telomeres consist of up to about 2500 repeats of the sequence 5'-TTAGGG-3' (SEQ ID NO:1). Telomeres in normal non-cancerous cells shorten each time that a cell divides. This has been viewed as a type of 'clock', helping to determine the lifespan of a cell population.

Several types of cells are "immortal". These include germline cells, unicellular eukaryotes, and certain cancer cells. These types of cells are able to maintain the length of their telomeres by the use of an enzyme. Telomerase is an enzyme that catalyzes the addition of a specific repeating DNA sequence onto the 3' end of DNA strands, thereby lengthening the telomere. The telomerase activity allows cells to compensate for telomere shortening that occurs during DNA replication. Telomerase activity is not detected in most normal somatic cells.

A connection between telomeres and aging was established by Bodnar et al. (*Science,* 279: 349-352, 1998). Transfection of a telomerase-encoding vector into telomerase-negative retinal pigment epithelial cells and foreskin fibroblasts showed dramatic effects. While non-transfected cells exhibited typical telomere shortening and senescence, the transfected cells showed lengthened telomeres and reduced levels of β-galactosidase (a marker for senescence). Furthermore, the transfected cells were reported to exceed their normal lifespan by at least 20 doublings.

Nakamura et al. (*Science* 277: 955-959, 1997) reported the isolation and sequencing of the human telomerase reverse transcriptase (hTERT) gene. Expression of hTERT mRNA corresponded with telomerase activity in cells. Meyerson et al. (*Cell* 90: 785-795, 1997) reported that hTERT (hEST2) is expressed at high levels in primary tumors, cancer cell lines, and telomerase-positive tissues but is undetectable in telomerase-negative cell lines and differentiated telomerase-negative tissues. Introduction of a nucleic acid sequence encoding the hTERT protein into mortal cells was shown to produce active telomerase (Weinrich, S. L., et al., *Nat. Genet.* 17(4): 498-502, 1997).

Interestingly, telomeres can be maintained in certain human cells that lack telomerase. An alternative pathway involving recombination has been found to be operative in several types of eukaryotes. In addition, a rolling circle mechanism has been suggested as providing a different alternative biological pathway for elongation of telomere repeat length (McEachern, M. J. et al., *Annu. Rev. Genet.* 34(1): 331-358, 2000). Extrachromosomal telomeric DNAs that may be present in circular form have been reported to be isolated from eukaryotic cells (Regev, A. et al., *Oncogene* 17: 3455-3461, 1998). However, this mechanism has not yet been proven, and it is not clear how such large double-stranded circles could initiate telomere extension, nor is it clear how such double stranded circles containing only telomere sequences could be synthesized.

The understanding of telomerase activity has led to two prospective applications: to increase the lifespan of non-immortal cells, and to kill cancerous immortal cells. Attempts to achieve both results have traditionally focused on upregulating or downregulating the telomerase enzyme itself.

Recently, attention has been turned towards potential chemical methods for achieving either goal (Cech, T. R., *Angew. Chem. Int. Ed. Engl.* 39(1): 34-43, 2000). Chemicals which regulate telomerase activity could be used as a potential cancer therapeutic or for increasing the replicative lifespan of a normal cell population. However, to date no such chemicals have been reported.

"Rolling circle" DNA replication is based on the observation that small circular DNA molecules act as efficient templates for DNA polymerases (Fire, A. and Xu, S. Q., *Proc. Natl. Acad. Sci. U.S.A.* 92(10): 4641-4645, 1995; Liu, D. Y. et al., *J. Am. Chem. Soc.* 118(7): 1587-1594, 1996). Rolling circle replication had previously been reported in bacteriophage DNA amplification (Nakai, H., *J. Biol. Chem.* 268(32): 23997-4004, 1993).

Rolling circle transcription has further been used, with RNA polymerases, to produce catalytic RNAs and circular RNAs (Sarah L. Daubendiek, S. L. and Kool, E. T., *Nature Biotech.* 15: 273-277, 1997; Diegelman, A. M. and Kool, E. T., *Nucleic Acids Res.* 26: 3235-3241, 1998; Daubendiek, S. L. et al., *J. Am. Chem. Soc.* 117: 7818-7819, 1995).

Rolling circle amplification (RCA) has been used in vitro for the linear or geometric amplification of circular oligonucleotide probes (Andras, S. C. et al., *Mol. Biotechnol.* 19(1): 29-44, 2001). Recently, rolling circles have been reported as being useful for detecting gene copy number and point mutations in fixed cells (Christian, A. T. et al., *Proc. Natl. Acad. Sci. U.S.A.* 98(25): 14238-14243, 2001).

U.S. Pat. No. 6,096,880 (issued Aug. 1, 2000) and U.S. Pat. No. 5,714,320 (issued Feb. 3, 1998) describe the use of a single stranded circular oligonucleotide template and an RNA polymerase to produce an RNA multimer. The multimers are suggested as being useful for diagnostic and/or therapeutic applications. U.S. Pat. No. 6,077,668 (issued Jun. 20, 2000) describes the labeling of such multimers and their use in diagnostic applications. The above multimers do not use primers, and the circles do not contain repeating sequences.

U.S. Pat. No. 5,872,105 (issued Feb. 16, 1999) describes single stranded DNA circles, and their potential uses. The circles bind both single- and double-stranded DNA molecules, and have potential use as a drug delivery device. Circular DNA molecules have further been shown to form triplex structures upon binding to a target sequence (U.S. Pat. No. 5,683,874, issued Nov. 4, 1997). However, no circles encoding telomeric DNA sequences were contemplated, and methods for making such repeating-sequence circles were not known. Standard methods for synthesis of DNA circles are not successful for circles containing repeating sequences.

The telomerase enzyme and telomere elongation has been proposed as a possible therapeutic method in: treating aging skin (Funk, W. D. et al., *Exp. Cell Res.* 258: 270-278, 2000), treating pancreatic cells (Funk, W. D. et al., *J. Endocrinol.* 166: 103-109, 2000), and in bone marrow transplantation (Lee, J. et al., *Bone Marrow Transplant* 24: 411-415, 1999; Engelhardt, M. et al., *Blood* 90: 182-193, 1997). However, permanent telomerase expression may lead to an elevated cancer risk (Hahn, W. C. et al., *Nature* 400: 464-468, 1999; Yaswen, P. et al., *J. Mamm. Gland Biol.* 6: 223-224, 2001).

Mutant telomeres have been discussed as a possible anti-cancer therapeutic (Kim, M. M. et al., *Proc. Natl. Acad. Sci U.S.A.* 98: 7982-7987, 2001). In order to use a mutant telomerase in an anticancer role, the sequence encoding the wild type telomerase RNA would have to be interrupted (likely via a "knock-out"), and a sequence encoding a mutant telomerase RNA would have to be introduced into the cell. This is difficult, and likely impractical in a clinical setting.

Small nucleic acid circles containing telomere repeats from the organism *Oxytricha* have been reported for use in structural studies (Chen, J. et al., *Chem. Commun.* 22: 2686-2687, 2002; *J. Am. Chem. Soc.* 123: 12901, 2001). A "G-quadruplex" was used to effect ligation of linear molecules into circular DNA. The circles are too small to effect telomere extension, and do not contain human telomere sequences. No use with polymerases was contemplated, and the methods for making them would not succeed with larger circles containing human sequences.

Double-stranded plasmid DNAs containing telomeric sequence were studied recently with the organism *Kluyveromyces lactis* (Natarajan, S. and McEachem, M. J. *Mol. Cell. Biol.* 22: 4512-4521, 2002). Those circular plasmids were shown to cause the telomeres to become lengthened by combined mechanisms involving integration, recombination, and rolling circle replication. The telomeric sequence was only a fraction of the total sequence of the plasmids. No plasmids of purely telomeric sequence were contemplated, and no single stranded DNAs were contemplated. The methods provided would not allow for either of these to be constructed. DNA circles that contain non-telomeric sequence would in many cases be undesirable because they cause unnatural non-telomeric sequences to be included in the extended telomere. Double-stranded circles would in many cases be undesirable because they could not hybridize to a telomeric end without being unwound.

Despite the considerable research reported to date, there still exists a need for effective therapeutic compositions and methods. The use of telomerase to extend telomeres is expensive due to the costs involved in obtaining the enzyme. Therapy with telomerase is also a poor method for clinical uses, as overexpression and permanent expression of the enzyme has been associated with an elevated cancer risk, and gene therapy is still highly risky and largely unproven in humans. The engineering of a mutant telomerase to eliminate cancer is technically challenging and likely impractical. Compositions and methods are needed that are both cost- and clinically-effective.

SUMMARY OF THE INVENTION

The present invention provides telomere-encoding nanocircles, methods for their preparation, and methods for their use. The nanocircles can comprise, consist essentially of, or consist of multiple repeats of the complement of telomere repeat sequences. Of particular interest are nanocircles that contain multiple repeats of the complement of the human telomere repeat sequence. Circular DNAs that have been reported in the scientific literature and in patents did not contain multiple repeats of the complement of telomere repeat sequences, and the synthetic methods previously reported are not effective at producing such nanocircles. No use of telomere-encoding nanocircles for telomere extension was previously contemplated.

The nanocircles can be used as templates for polymerases to make or to extend new telomere sequences on an existing DNA or RNA molecule. They can be used to extend the lifespan of normal cell populations, and can also be used to induce apoptosis and death in cancerous cells. Applications are disclosed for the extension of telomeres or telomere primers under both in vitro and in vivo conditions. The nanocircles can be used in living cells, and when so used may function without the addition of polymerase or nucleotides due to the presence of polymerase and nucleotides in the cells.

Biomedical and therapeutic applications such as the treatment of macular degeneration, treating the effects of skin aging, treating liver degeneration, and both in vitro and in vivo anti-cancer applications are disclosed. Additionally, the use of nanocircles in the treatment of primary cells outside of the body for extension of lifespan of the cell population is disclosed.

The telomere-encoding nanocircles are easier to produce and to store than telomerase enzyme. Because they are much smaller than plasmids, they can be readily synthesized in large quantities and in any sequence using a DNA synthesizer. Because they can be constructed to contain only telomere sequence, they can uniquely catalyze the extension of purely natural teloemric sequences. In addition, they can be designed to add non-natural sequences to a telomere or to a telomere sequence primer. They can be used to extend the length of telomeres on natural or artificial chromosomes. Nanocircles can be used to treat cancer without requiring genetic engineering of the cancer cells. These nanocircles can be used to extend the lifespan of non-cancerous cell populations in culture, providing enhanced materials for biomedical research, tissue engineering, and transplantation. Accordingly, nucleic acid nanocircles overcome many of the problems with the currently used compositions and methods.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIGS. 1A-1C show nanocircles encoding complement of human telomere repeat sequence.

DESCRIPTION OF THE SEQUENCE LISTINGS

The following sequence listings form part of the present specification and are included to further demonstrate certain aspects of the present invention. The invention may be better understood by reference to one or more of these sequences in combination with the detailed description of specific embodiments presented herein.

| SEQ ID NO: | Description |
|---|---|
| 1 | Overhanging strand of human telomere repeat sequence 5'-TTAGGG-3' |
| 2 | Overhanging strand of yeast telomere repeat sequence 5'-TGTGGG-3' |
| 3 | Human nanocircle DNA repeating unit 5'-CCCTAA-3' |
| 4 | Human nanocircle RNA repeating unit 5'-CCCUAA-3' |
| 5 | Yeast nanocircle DNA repeating unit 5'-CCCACA-3' |
| 6 | 5'-dAGG GTG TGG GTG TGG GTT AG-3' |
| 7 | d(CAGAT) |
| 8 | d(CAGdmaAT) |
| 9 | d(acCpacAipr-pacGdmaAT) |
| 10 | d(CAGdmaAT) |
| 11 | 5'-TTAGGGTTAGGGTTAGGG-3' |
| 12 | HT42 precircle; 5'-pd(pacApacAC CCT pacApacAC CCT dmaAdmaAC CCT dmaAdmaAC CCT dmaAdmaAC CCT dmaAdmaAC CCT pacApacAC CCT)-3' where all Cs are protected by acetyl groups |
| 13 | HT42 splint; 5'-dGGTTAGGGTTAGGGTTAGGG-3' |
| 14 | HT54 precircle; 5'-pd(pacApacAC CCT pacApacAC CCT dmaAdmaAC CCT dmaAdmaAC CCT dmaAdmaAC CCT dmaAdmaAC CCT dmaAdmaAC CCT dmaAdmaAC CCT pacApacAC CCT)-3' where all C's are protected by acetyl groups |
| 15 | HT54 splint; 5'-GTTAGGGTTAGGGTTAGG-3' |
| 16 | HT72 precircle; 5'-pd(pacApacAC CCT pacApacAC CCT dmaAdmaAC CCT dmaAdmaAC CCT dmaAdmaAC CCT dmaAdmaAC CCT dmaAdmaAC CCT dmaAdmaAC CCT dmaAdmaACC CT dmaAdmaAC CCT dmaAdmaAC CCT pacApacAC CCT)-3' where all Cs are protected by acetyl groups |
| 17 | HT72 splint; 5'-dGGTTAGGGTTAGGGTTAGGG-3' |
| 18 | YT54 precircle; 5'-pd(CCC ACA CCC TAA CCC TAA CCC TAA CCC TAA CCC TAA CCC TAA CCC ACA)-3' |
| 19 | YT54 splint; 5'-dAGGGTGTGGGTGTGGGTTAG-3' |
| 20 | YT54SC precircle; 5'-pd(CAC TCC ACT CCA CAC CTC ACC AAA CTC CAC AAC CAC AAC ACC ACA CTC ACT CCT)-3' |
| 21 | YT54SC splint; 5'-dGAGTGGAGTGAGGAGTGAGT-3' |

-continued

Figure 1C:
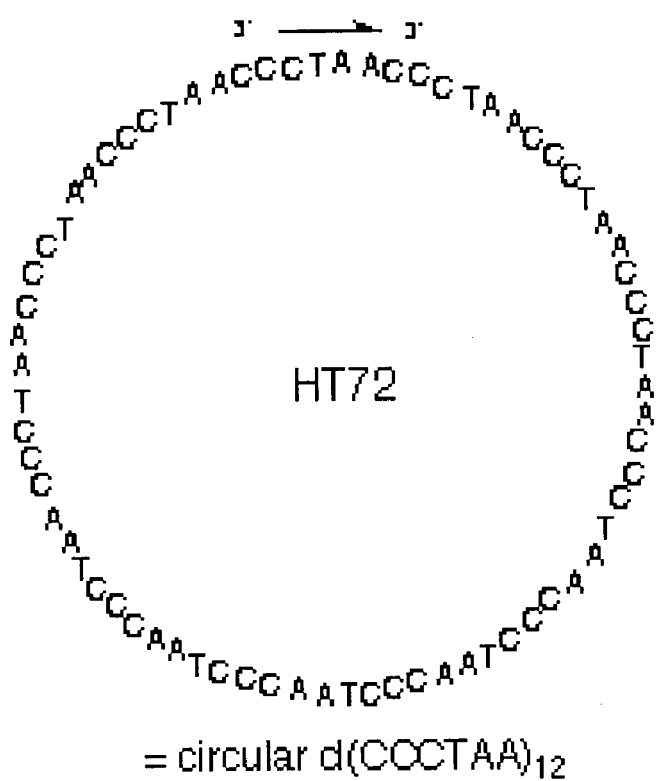
Figure 1D:
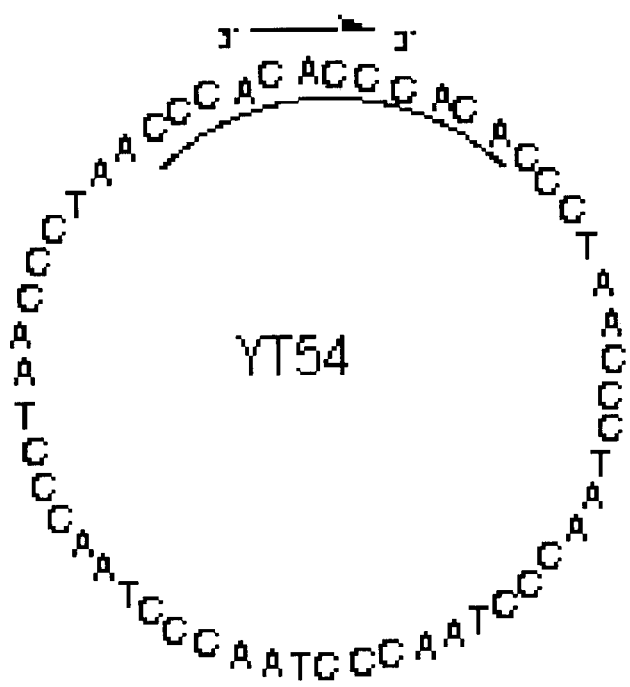
FIGS. 1D-1F show chimeric nanocircle and scrambled nanocircles.
Figure 1E:
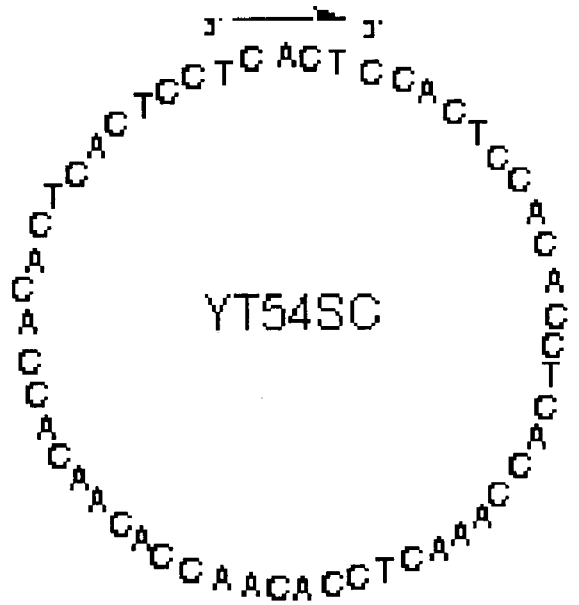
Figure 1F:
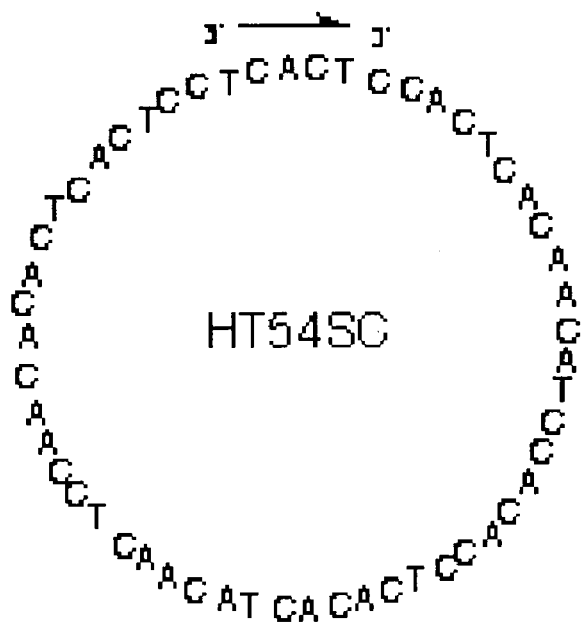
Figure 1G:
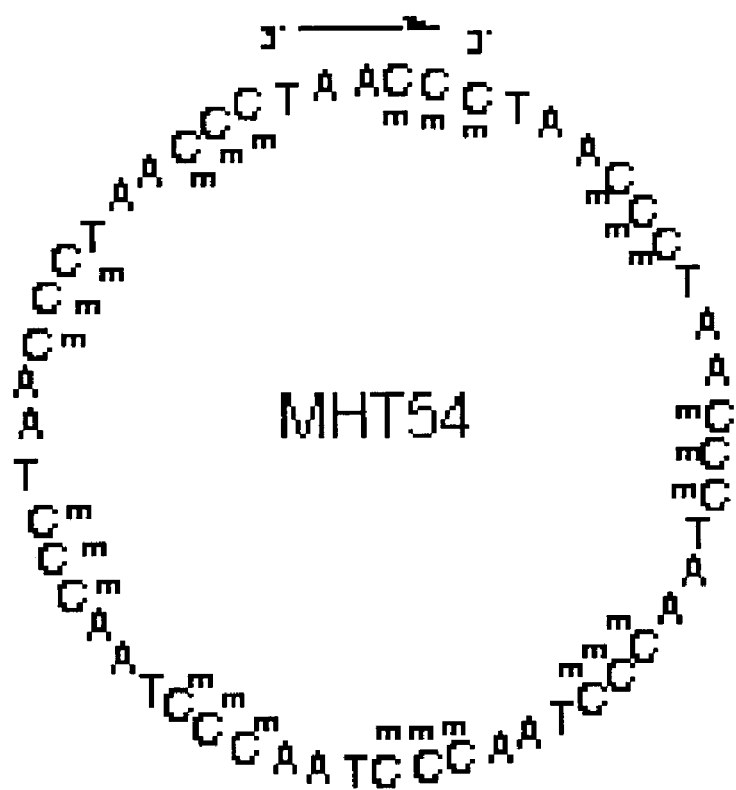
FIG. 1G shows a nanocircle useful for stronger hybridization.
Figure 2A:
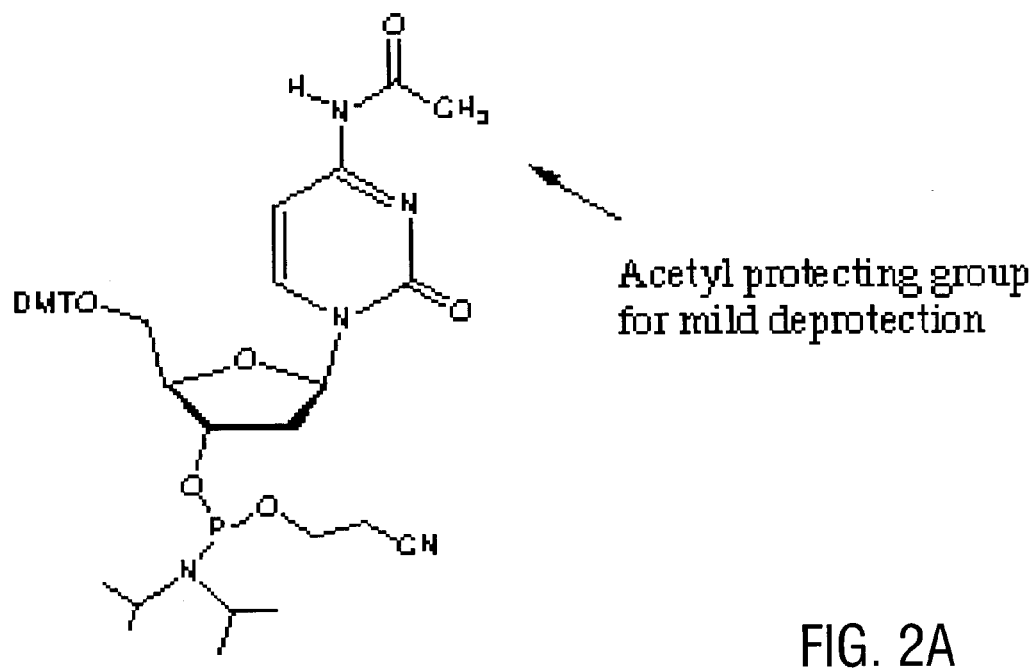
FIGS. 2A-2D illustrate orthogonal protecting group chemistry.
Figure 2B:
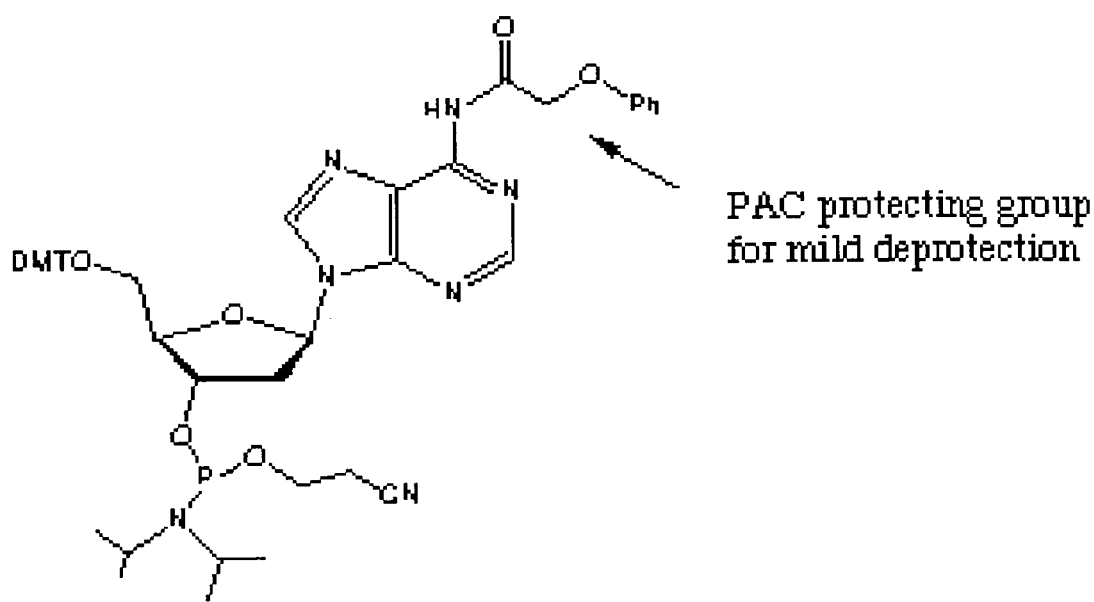
Figure 2C:
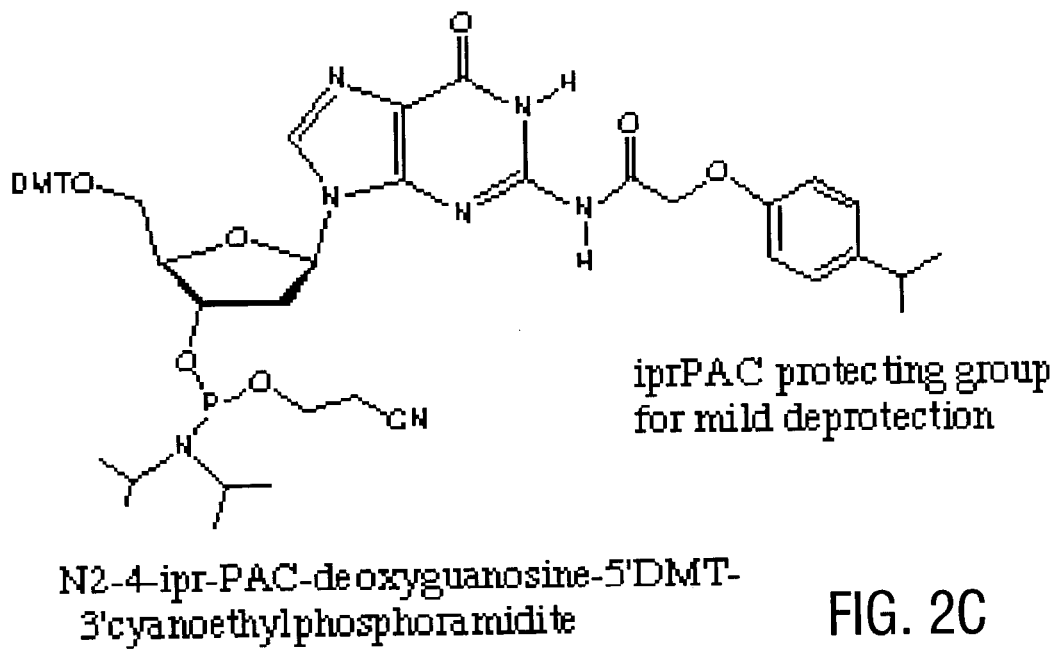
Figure 2D:
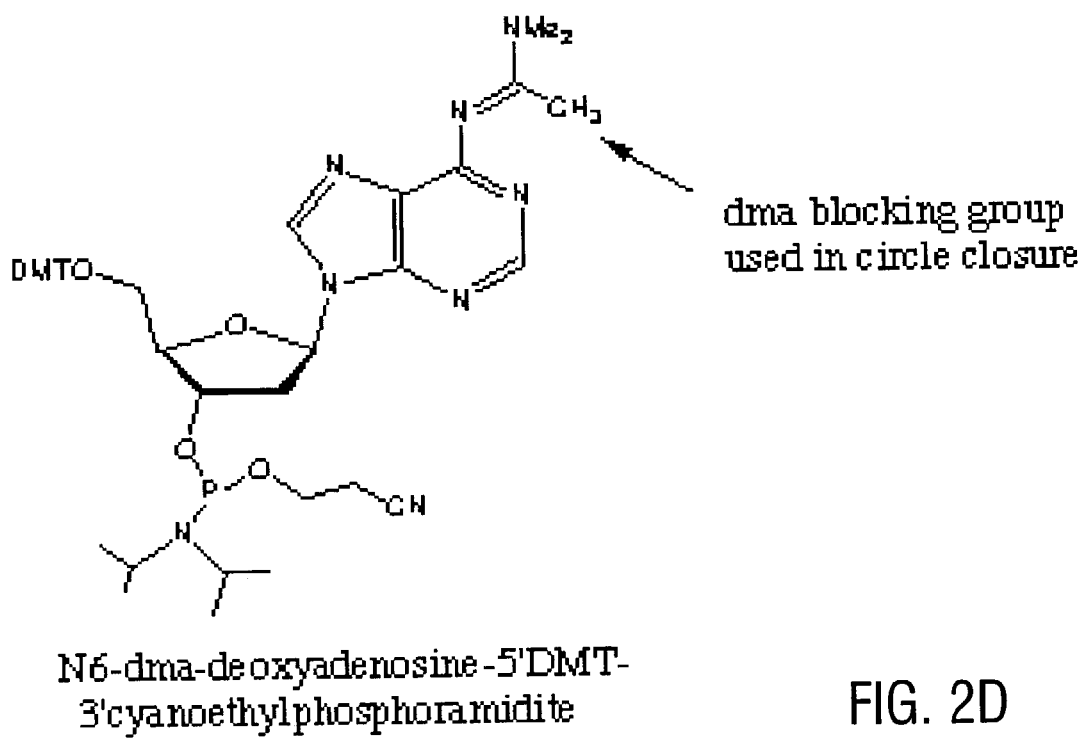

| SEQ ID NO: | Description |
|---|---|
| 22 | HT54SC precircle; 5'-pd(CAC TCC ACT CAC AAC ATC CAC ACC TCA CAC TAC AAC TCC AAC ACA CTC ACT CCT)-3' |
| 23 | HT54SC splint; 5'-dGTGTGGAGTGAGGAGTGAGT-3' |
| 24 | MHT54 precircle; 5'-pd(pacApacAmC mCmCT pacApacAmC mCmCT dmaAdmaAmC mCmCT dmaAdmaAmC mCmCT dmaAdmaAmC mCmCT dmaAdmaAmC mCmCT dmaAdmaAmC mCmCT dmaAdmaAmC mCmCT pacApacAmC mCmCT) where mC is 5'-methylC, and where all mCs are protected by acetyl groups |
| 25 | MHT54 splint; 5'-dGGTTAGGGTTAGGGTTAGGG-3' |
| 26 | HT30 nanocircle; circular d(CCCTAA)$_5$ = d(CCTAAC)$_5$ = d(CTAACC)$_5$ = d(TAACCC)$_5$ = d(AACCCT)$_5$ = d(ACCCTA)$_5$ |
| 27 | HT36 nanocircle; circular d(CCCTAA)$_6$ = d(CCTAAC)$_6$ = d(CTAACC)$_6$ = d(TAACCC)$_6$ = d(AACCCT)$_6$ = d(ACCCTA)$_6$ |
| 28 | HT42 nanocircle; circular d(CCCTAA)$_7$ = d(CCTAAC)$_7$ = d(CTAACC)$_7$ = d(TAACCC)$_7$ = d(AACCCT)$_7$ = d(ACCCTA)$_7$ |
| 29 | HT48 nanocircle; circular d(CCCTAA)$_8$ = d(CCTAAC)$_8$ = d(CTAACC)$_8$ = d(TAACCC)$_8$ = d(AACCCT)$_8$ = d(ACCCTA)$_8$ |
| 30 | HT54 nanocircle; circular d(CCCTAA)$_9$ = d(CCTAAC)$_9$ = d(CTAACC)$_9$ = d(TAACCC)$_9$ = d(AACCCT)$_9$ = d(ACCCTA)$_9$ |
| 31 | HT60 nanocircle; circular d(CCCTAA)$_{10}$ = d(CCTAAC)$_{10}$ = d(CTAACC)$_{10}$ = d(TAACCC)$_{10}$ = d(AACCCT)$_{10}$ = d(ACCCTA)$_{10}$ |
| 32 | HT66 nanocircle; circular d(CCCTAA)$_{11}$ = d(CCTAAC)$_{11}$ = d(CTAACC)$_{11}$ = d(TAACCC)$_{11}$ = d(AACCCT)$_{11}$ = d(ACCCTA)$_{11}$ |
| 33 | HT72 nanocircle; circular d(CCCTAA)$_{12}$ = d(CCTAAC)$_{12}$ = d(CTAACC)$_{12}$ = d(TAACCC)$_{12}$ = d(AACCCT)$_{12}$ = d(ACCCTA)$_{12}$ |
| 34 | HT78 nanocircle; circular d(CCCTAA)$_{13}$ = d(CCTAAC)$_{13}$ = d(CTAACC)$_{13}$ = d(TAACCC)$_{13}$ = d(AACCCT)$_{13}$ = d(ACCCTA)$_{13}$ |
| 35 | YT54 human$_7$ yeast$_2$ nanocircle; circular d((CCCTAA)$_7$(CCCACA)$_2$) |
| 36 | YT54SC nanocircle (scrambled version of YT54); circular 5'-dCAC TCC ACT CCA CAC CTC ACC AAA CTC CAC AAC CAC AAC ACC ACA CTC ACT CCT-3' (see FIG. 1B) |
| 37 | HT54SC nanocircle (scrambled version of HT54); circular 5'-dCAC TCC ACT CAC AAC ATC CAC ACC TCA CAC TAC AAC TCC AAC ACA CTC ACT CCT-3' (see FIG. 1B) |
| 38 | MHT54 nanocircle; circular d(mCmCmCTAA)$_9$; mC = 5-methylC (see FIG. 1C) |
| 39 | Telomere repeat sequence 5'-TTGGGG-3' |
| 40 | Telomere repeat sequence 5'-TT(T/G)GGG-3' |
| 41 | Telomere repeat sequence 5'-TTTTGGGG-3' |
| 42 | Telomere repeat sequence 5'-A(G)$_{1-8}$-3' |
| 43 | Telomere repeat sequence 5'-TAGGG-3' |
| 44 | Telomere repeat sequence 5'-TT(T/C)AGGG-3' |
| 45 | Telomere repeat sequence 5'-TG$_{2-3}$(TG)$_{1-6}$-3' |
| 46 | Telomere repeat sequence 5'-TTACA(G)$_{2-5}$-3' |
| 47 | Telomere repeat sequence 5'-ACGGATGTCTAACTTCTTGGTGT-3' |
| 48 | Telomere repeat sequence 5'-ACGGATTTGATTAGGTATGTGGTGT-3' |
| 49 | Telomere repeat sequence 5'-CTGGGTGCTGTGGGGT-3' |
| 50 | Telomere repeat sequence 5'-GGGGTCTGGGTGCT-3' |

-continued

| SEQ ID NO: | Description |
|---|---|
| 51 | Telomere repeat sequence 5'-GGTGTACGGATGTCTAACTTCT-3' |
| 52 | Telomere repeat sequence 5'-GGTGTA(C/A)GGATGTCACGATCAT-3' |
| 53 | Telomere repeat sequence 5'-GGTGTACGGATGCAGACTCGCTT-3' |
| 54 | Telomere repeat sequence 5'-TTA(G)$_{4-6}$-3' |
| 55 | Telomere repeat sequence 5'-TTAGGC-3' |
| 56 | Telomere repeat sequence 5'-TTGCA-3' |
| 57 | Telomere repeat sequence 5'-TTAGG-3' |
| 58 | Telomere repeat sequence 5'-TTTTAGGG-3' |
| 59 | Telomere repeat sequence 5'-TT(T/A)GGG-3' |
| 60 | Primer 5'-d(TTAGGG)$_3$-3' |
| 61 | C rich primer 5'-d(CCCTAA)$_3$-3' |
| 62 | Nanocircle; circular d(TTAGGG)$_9$; complement of HT54 nanocircle |
| 63 | Human DNA repeating unit 5'-TTAGGG-3' (complement of SEQ ID NO:3) |
| 64 | Human RNA repeating unit 5'-UUAGGG-3' (complement of SEQ ID NO:3) |

DEFINITIONS

The following definitions are provided in order to aid those skilled in the art in understanding the detailed description of the present invention.

"Complement" refers to a nucleic acid sequence that specifically hybridizes to a particular sequence, using A/T and G/C pairings in antiparallel orientation. For example, the complement of 5'-TTAGGG-3' (SEQ ID NO:1) is 5'-CCCTAA-3' (SEQ ID NO:3).

"DMA" refers to the dimethylacetamidine chemical protecting group. In the nucleic acid sequences shown herein, the protecting group precedes the nucleotide to which it is attached.

"In vitro" telomere extension is meant to encompass treatment of telomeres or telomere primers in the absence of cells.

"In vivo" telomere extension is meant to encompass treatment of cells and cell cultures (sometimes referred to as ex vivo), and treatment of organisms.

"Nucleic acid nanocircle" refers to a circular topology nucleic acid molecule.

"PAC" or "pac" refers to the phenoxyacetyl chemical protecting group. "Ipr-PAC" refers to the isopropylphenoxyacetyl chemical protecting group. In the nucleic acid sequences shown herein, the protecting group precedes the nucleotide to which it is attached.

"Telomere repeat sequence" refers to nucleic acid sequences found in multiple adjacent repeats in a telomere. Different organisms have different telomere repeat sequences. In human telomeres, the telomere repeat sequence is 5'-TTAGGG-3' (SEQ ID NO:1). See Table 1 below for a listing of telomere repeat sequences from various organisms.

"TEN" refers to a telomere encoding nanocircle, while "MTEN" refers to a mutant telomere encoding nanocircle.

DETAILED DESCRIPTION OF THE INVENTION

Telomere Repeat Sequences

Different organisms have different telomere repeat sequences. Any of the following repeat sequences can be used in the design, construction, and use of nucleic acid nanocircles.

TABLE 1

| | | Telomere repeat sequences | |
|---|---|---|---|
| Family | Organism | | Sequence |
| Ciliata | Tetrahymena | TTGGGG | (SEQ ID NO:39) |
| | Glaucoma | TTGGGG | (SEQ ID NO:39) |
| | Paramecium | TT(T/G)GGG | (SEQ ID NO:40) |
| | Oxytrichia | TTTTGGGG | (SEQ ID NO:41) |
| | Stylonychia | TTTTGGGG | (SEQ ID NO:41) |
| | Euplotes | TTTTGGGG | (SEQ ID NO:41) |

TABLE 1-continued

Telomere repeat sequences

| Family | Organism | Sequence | |
|---|---|---|---|
| Myxomycetes | *Physarum* | TTAGGG | (SEQ ID NO:1) |
| | *Dictyostelium* | A(G)$_{1-8}$ | (SEQ ID NO:42) |
| | *Didymium* | TTAGGG | (SEQ ID NO:1) |
| Flagella | *Trypanosoma* | TTAGGG | (SEQ ID NO:1) |
| | *Crithidia* | TTAGGG | (SEQ ID NO:1) |
| | *Giardia* | TAGGG | (SEQ ID NO:43) |
| Sporozzooa | *Plasmodium* | TT(T/C)AGGG | (SEQ ID NO:44) |
| Fungi | *Cladosporium fulvum* | TTAGGG | (SEQ ID NO:1) |
| | *Neurospora* | TTAGGG | (SEQ ID NO:1) |
| | *Podospora* | TTAGGG | (SEQ ID NO:1) |
| | *Histoplasma* | TTAGGG | (SEQ ID NO:1) |
| | *Saccharomyces cerevisiae* | TG$_{2-3}$(TG)$_{1-6}$ | (SEQ ID NO:45) |
| | *Schizosaccharomyces pombe* | TTACA(G)$_{2-5}$ | (SEQ ID NO:46) |
| | *Candida albicans* | ACGGATGTCTAACTTCTTGGTGT | (SEQ ID NO:47) |
| | *Kluyveromyces lactis* | ACGGATTTGATTAGGTATGTGGTGT | (SEQ ID NO:48) |
| | *Candida glabrata* | CTGGGTGCTGTGGGGT | (SEQ ID NO:49) |
| | *Candida tropicalis* | GGGGTCTGGGTGCT | (SEQ ID NO:50) |
| | *Candida maltosa* | GGTGTACGGATGTCTAACTTCT | (SEQ ID NO:51) |
| | *Candida guillermondii* | GGTGTA(C/A)GGATGTCACGATCAT | (SEQ ID NO:52) |
| | *Candida pseudotropicalis* | GGTGTACGGATGCAGACTCGCTT | (SEQ ID NO:53) |
| | *Cryptococcus neoformans* | TTA(G)$_{4-6}$ | (SEQ ID NO:54) |
| Nemathelminth | *Ascaris lumbricoides* | TTAGGC | (SEQ ID NO:55) |
| | *Parascaris univalens* | TTGCA | (SEQ ID NO:56) |
| | *Caenorhabditis elegans* | TTAGGC | (SEQ ID NO:55) |
| Insecta | *Bombyx mori* | TTAGG | (SEQ ID NO:57) |
| Algae | *Chlamydomonas* | TTTTAGGG | (SEQ ID NO:58) |
| Higher plants | *Arabidopsis* | TTTAGGG | (SEQ ID NO:1) |
| | *Tomato* | TT(T/A)GGG | (SEQ ID NO:59) |
| Vertebrata | *Homo sapiens* | TTAGGG | (SEQ ID NO:1) |
| | *Mus sp.* | TTAGGG | (SEQ ID NO:1) |
| | *Xenopus* | TTAGGG | (SEQ ID NO:1) |

Nucleic Acid Nanocircles

One embodiment of the invention is directed towards nucleic acid nanocircles comprising at least two repeats of the complement of a telomere repeat sequence. The telomere repeat sequence can generally be any telomere repeat sequence found in any organism. For example, the complement of a telomere repeat sequence can be 5'-CCCTAA-3' (SEQ ID NO:3) or 5'-CCCUAA-3' (SEQ ID NO:4). The nanocircle can generally be any number of nucleotides in length (measured in nucleotide bases if single stranded, nucleotide base pairs if double stranded). It is currently preferred that the nanocircles be up to about 2004 nucleotides in length. It is currently preferred but not required that the length of the nanocircle be an integer multiple of the length of the telomere repeat sequence. For example, if a telomere repeat sequence is six nucleotides long (such as in SEQ ID NO:1), it is currently preferred but not required that the length of the nanocircle be a multiple of 6 (i.e. the length can evenly be divided by 6). Various ranges of length include 20-2000, 30-600, 30-300, and 36-78 nucleotides. Specific lengths in the range of 30-78 nucleotides include 30, 36, 42, 48, 54, 60, 66, 72, and 78 nucleotides (all evenly divisible by six). The nanocircles can be DNA nanocircles or RNA nanocircles. The nanocircles can be single stranded or double stranded. Alternatively, nucleic acid nanocircles can be made comprising at least two repeats of a telomere sequence (i.e. the complement of the above described nucleic acid nanocircles).

An additional embodiment of the invention is directed towards a nucleic acid nanocircle comprising at least 2 repeats of a telomere repeat sequence, wherein at least 50% of the sequence of the nanocircle is an integral number of telomere repeat sequence repeats. For example, a nucleic acid nanocircle can comprise at least 2 repeats of 5'-TGTGGG-3' (SEQ ID NO:2), at least 2 repeats of 5'-CCCTAA-3' (SEQ ID NO:3), at least 2 repeats of 5'-CCCUAA-3' (SEQ ID NO:4), at least 2 repeats of 5'-CCCACA-3' (SEQ ID NO:5), at least 2 repeats of 5'-TTAGGG-3' (SEQ ID NO:63), or at least 2 repeats of 5'-UUAGGG-3' (SEQ ID NO:64), wherein: at least about 50% of the sequence of the nanocircle is an integral number of repeats of 5'-TGTGGG-3' (SEQ ID NO:2), at least about 50% of the sequence of the nanocircle is an integral number of repeats of 5'-CCCTAA-3' (SEQ ID NO:3); at least about 50% of the sequence of the nanocircle is an integral number of repeats of 5'-CCCUAA-3' (SEQ ID NO:4), at least about 50% of the sequence of the nanocircle is an integral number of repeats of 5'-CCCACA-3' (SEQ ID NO:5), at least about 50% of the sequence of the nanocircle is an integral number of repeats of 5'-TTAGGG-3' (SEQ ID NO:63), or at least about 50% of the sequence of the nanocircle is an integral number of repeats of 5'-UUAGGG-3' (SEQ ID NO:64). The percentage can be at least about 50%, at least about 60%, at least about 70%, at least about 80%, at least about 90%, at least about 92%, at least about 94%, at least about 96%, at least about 98%, or about 100%. For example, a nucleic acid nanocircle of 2000 bases in length containing 640 repeats of SEQ ID NO:3 has a calculated percentage of 96% (640×6/2000), whereas the same nanocircle containing 240 repeats of SEQ ID NO:3 has a calculated percentage of 72% (240×6/2000). The nanocircle can generally be of any length. The nanocircle can generally be any number of nucleotides in length (measured in nucleotide bases if single stranded, nucleotide base pairs if double stranded). It is currently preferred that the nanocircles be up to about 2004 nucleotides in length. It is presently preferred, but not required, that the nanocircles be single-stranded.

A further embodiment of the invention is directed towards a nucleic acid nanocircle consisting essentially of at least two repeats of a telomere repeat sequence. For example, the nanocircle can consist essentially of: at least 2 repeats of 5'-TGTGGG-3' (SEQ ID NO:2), at least two repeats of 5'-CCCTAA-3' (SEQ ID NO:3); at least two repeats of 5'-CCCUAA-3' (SEQ ID NO:4), at least two repeats of 5'-CCCACA-3' (SEQ ID NO:5), at least 2 repeats of 5'-TTAGGG-3' (SEQ ID NO:63), or at least 2 repeats of 5'-UUAGGG-3' (SEQ ID NO:64). The nanocircle can generally be any number of nucleotides in length (measured in nucleotide bases if single stranded, nucleotide base pairs if double stranded). It is currently preferred that the nanocircles be up to about 2004 nucleotides in length.

An additional embodiment of the invention is directed towards a nucleic acid nanocircle consisting of an integral number of telomere repeat sequences (for example, see FIG. 1A). The telomere repeat sequence can generally be any telomere repeat sequence found in any organism. For example, the telomere repeat sequence can be 5'-TGTGGG-3' (SEQ ID NO:2), 5'-CCCTAA-3' (SEQ ID NO:3), 5'-CCCUAA-3' (SEQ ID NO:4), 5'-CCCACA-3' (SEQ ID NO:5), 5'-TTAGGG-3' (SEQ ID NO:63), or 5'-UUAGGG-3' (SEQ ID NO:64). The nanocircle can generally be any number of nucleotides in length (measured in nucleotide bases if single stranded, nucleotide base pairs if double stranded). It is currently preferred that the nanocircles be up to about 2004 nucleotides in length. Specific examples of such nanocircles are HT30 (SEQ ID NO:26), HT36 (SEQ ID NO:27), HT42 (SEQ ID NO:28), HT48 (SEQ ID NO:29), HT54 (SEQ ID NO:30), HT60 (SEQ ID NO:31), HT66 (SEQ ID NO:32), HT72 (SEQ ID NO:33), and HT78 (SEQ ID NO:34). The nanocircles can be DNA nanocircles or RNA nanocircles. The nanocircles can be single stranded or double stranded. Alternatively, nucleic acid nanocircles can be made consisting of an integral number of repeats of the complement of a telomere repeat sequence (i.e. the complement of the above described nucleic acid nanocircles).

Methods of Preparation

The invention is also directed towards methods of preparing nucleic acid nanocircles. The prepared nucleic acid nanocircles can consist of an integral number of repeats of a nucleic acid sequence, but are not required to be so. The method can comprise obtaining a protected linear precursor nucleic acid molecule having: a first protecting group attached to one or more nucleotides at or near the 5' end of the linear precursor nucleic acid molecule, a second protecting group attached to one or more nucleotides at or near the 3' end of the linear precursor nucleic acid molecule, and at least one third protecting group attached to the linear precursor nucleic acid molecule between the 5' end and the 3' end of the linear precursor nucleic acid molecule; treating the protected linear precursor nucleic acid molecule under conditions suitable to remove the first protecting group and the second protecting group from the protected linear precursor nucleic acid molecule to produce a partially deprotected linear precursor nucleic acid molecule; contacting the partially deprotected linear precursor nucleic acid molecule with a splint nucleic acid molecule to form a linear/splint complex, wherein the splint nucleic acid molecule binds to both the 5' end and to the 3' end of the partially deprotected linear precursor nucleic acid molecule; contacting the linear/splint complex with a ligation agent to produce a partially protected nucleic acid nanocircle; and treating the partially protected nucleic acid nanocircle under conditions suitable to remove the third protecting group to produce the nucleic acid nanocircle (for example, see FIG. 3B). The first protecting group and second protecting group can be the same or different protecting groups. The protected linear precursor nucleic acid molecule can have one or more third protecting groups. The third protecting groups preferably serve to prevent the splint nucleic acid molecule from binding unproductively to the partially deprotected linear precursor nucleic acid molecule (i.e. in a manner that does not enable the ligase enzyme to ligate the 5' and 3' ends to produce the partially protected nucleic acid nanocircle precursor). The nanocircles can be DNA nanocircles or RNA nanocircles. The nanocircles can be single stranded or double stranded. The third protecting group and the combined first protecting group and second protecting group preferably deprotect under "orthogonal conditions", that is that the condition for removing the first protecting group and second protecting group does not effect removal of the third protecting group. For example, the first protecting group and second protecting group can be PAC, and the third protecting group can be DMA. The ligation agent can be an enzyme or chemicals. The enzyme can be a DNA ligase enzyme. The chemical ligation agents can generally be any chemicals that cause DNA ligation. Examples include cyanogen bromide, N-cyanoimidazole, EDC, and water soluble carbodiimides. The integral number of repeats of the nucleic acid sequence can generally be of any nucleic acid sequence. The nucleic acid sequence can be the complement of a telomere repeat sequence. Examples of these repeating sequences include 5'-TGTGGG-3' (SEQ ID NO:2), 5'-CCCTAA-3' (SEQ ID NO:3), 5'-CCCUAA-3' (SEQ ID NO:4), 5'-CCCACA-3' (SEQ ID NO:5), 5'-TTAGGG-3' (SEQ ID NO:63), and 5'-UUAGGG-3' (SEQ ID NO:64).

Methods of Use

Generally any of the above described nucleic acid nanocircles can be used in the following methods of Use.

In Vitro Telomere Extension Applications

Nucleic acid nanocircles can be used in methods to extend the length of a telomere primer (or telomere) in vitro. The methods can comprise selecting a telomere primer; and contacting the telomere primer with a nucleic acid nanocircle, a polymerase, and deoxyribonucleoside triphosphates under conditions suitable for polymerase activity. The selection step could involve obtaining a telomere, or obtaining a synthetic primer having a telomere sequence at its end. The length of the telomere primer after the contacting step is greater than the length of the telomere primer prior to the contacting step. The difference in length is preferably at least about 96 nucleotides. The difference can be at least about 1000, at least about 5000, at least about 10000, at least about 15000, at least about 20000, or at least about 25000 nucleotides. The telomere can be obtained from any organism. For example, the organism can be a human, yeast, cat, dog, cow, pig, horse, mouse, rat, insect, plant, ciliate, fungus, fish, or zebrafish. The telomere can be an isolated telomere, or attached to a chromosome. The chromosome can be from any organism, or can be prepared by methods known to those of skill in the art of artificial chromosome construction. For example, the chromosome can be a human, yeast, cat, dog, cow, pig, horse, mouse, rat, insect, plant, ciliate, fungus, fish, or zebrafish. The telomere primer can be attached to a human artificial chromosome. The polymerase can generally be any polymerase. The polymerase can be a DNA polymerase, an RNA polymerase, or a reverse transcriptase. For example, the polymerase can be DNA polymerase α, DNA polymerase β, the endonuclease free Klenow fragment of DNA polymerase I, T7 DNA polymerase, exonuclease free T7 DNA polymerase, φ29 DNA polymerase, Deep Vent DNA polymerase, Taq polymerase, or AMV reverse transcriptase.

Additionally, nucleic acid nanocircles can be used in methods to synthesize a telomere sequence on a substance containing a short "telomere primer". The substance can generally be any chemical, surface, or biomolecule. These can include small organic molecules, metal surfaces, glass surfaces, ceramic surfaces, proteins, nucleic acids, membranes, viruses, or any other material of interest. A telomere primer is a short nucleic acid sequence that binds to the nucleic acid nanocircle. The method can comprise selecting a substance containing a telomere primer, and contacting the substance with a nucleic acid nanocircle, a polymerase, and deoxyribonucleoside triphosphates under conditions suitable for polymerase activity. The polymerase can be a DNA polymerase, an RNA polymerase, or a reverse transcriptase. For example, the polymerase can be DNA polymerase α, DNA polymerase β, the endonuclease free Klenow fragment of DNA polymerase I, T7 DNA polymerase, exonuclease free T7 DNA polymerase, φ29 DNA polymerase, Deep Vent DNA polymerase, Taq polymerase, or AMV reverse transcriptase. The method can further comprise a detection step to detect the produced telomere sequence. These methods can accordingly be used as a diagnostic test for the substance.

Modified and/or Detectable Bases

Many different nucleoside triphosphates are suitable for use in the in vitro telomere extension methods. Generally, any nucleoside triphosphate that can be incorporated by the DNA polymerase or reverse transcriptase can be used. Examples of naturally occurring and synthetic nucleoside triphosphates include: ATP, dATP, CTP, dCTP, GTP, dGTP, TTP, dTTP, UTP, dUTP, 5-methyl-CTP, 5-methyl-dCTP, 5-bromo-CTP, 5-bromo-dCTP, ITP, dITP, 2-amino-adenosine-TP, 2-amino-deoxyadenosine-TP as well as the alpha-thiotriphosphates for all of the above, and 2'-O-methyl-ribonucleoside triphosphates for all the above bases. Other examples include 2'-fluoro-NTP, 2'-amino-NTP, 2'-fluoro-2'-deoxyribose, 2'-amino-2'-deoxyribose, 4'-methyl-2'-deoxyribose, 4'-ethyl-2'-deoxyribose, and 2'-O-methylribose. For incorporation of natural bases into DNA sequences, at least two nucleoside triphosphates are selected from dATP, dCTP, dGTP, dTTP, and mixtures thereof as is appropriate based on the telomere repeat sequence used. Modified bases can also be used such as 5-Br-UTP, 5-Br-dUTP, 5-F-UTP, 5-F-dUTP, 5-propynyl dCTP, and 5-propynyl-dUTP. Most of these nucleoside triphosphates are commercially available from sources such as Sigma Chemical Co. (St. Louis, Mo.).

The use of labeled nucleoside triphosphates allows for the preparation of a labeled or detectable telomere. Detection can be based on, for example, biotinylated bases, fluorescent bases, digoxigenin (DIG) labeled bases, or radioisotopes incorporated into the nucleoside triphosphates. The detection of these moieties is well known in the art.

Many different nucleosides are suitable for incorporation into the nucleic acid nanocircle itself. These include: T and analogs of T: e.g., rT, dT, rU, dU, 5-bromo-dU, 5-fluoro-dU, 5-chloro-dU, 5-iodo-dU, 5-bromo-U, 5-fluoro-U, 5-chloroU, 5-iodo-U, 5-propynyldU, 5-ethyl-dU, pseudo-dU, 2,4-difluoro-5-methylbenzene-2'-deoxyriboside, and 2,4-difluorobenzene-riboside; C and analogs of C: e.g., rC, dC, rC, dC, 5-bromo-dC, 5-fluoro-dC, 5-chlorodC, 5-iodo-dC, 5-bromo-C, 5-fluoro-C, 5-chloroC, 5-iodo-C, 5-propynyldC, 5-methyldC, 5-ethyldC, isoC, and iso-dC; A and analogs of A, e.g., rA, dA, 7-deaza-dA, 7-methyl-7-deaza-dA, 7-deaza-8-aza-dA, 7-iodo-7-deaza-dA, 7-bromo-7-deaza-dA, 7-iodo-7-deaza-dA, 7-chloro-7-deaza-dA, 7-propynyl-7-deaza-dA, 2-amino-dA; and G and analogs of G, e.g., rG, iso-dG, dG, 7-deaza-dG, 7-methyl-7-deaza-dG, 7-deaza-8-aza-dG, 7-iodo-7-deaza-dG, 7-bromo-7-deaza-dG, 7-iodo-7-deaza-dG, 7-chloro-7-deaza-dG, 7-propynyl-7-deaza-dG, dI, and rI. It is understood by those familiar with the art that the above modified nucleosides can be substituted for their natural analogs dT, dU, dC, dA, or dG in a telomere-encoding nanocircle.

Modified sugars and backbones that are a substrate for polymerase enzymes can be incorporated into the nanocircles. Modified sugars include 2'-fluoro-2'-deoxyribose, 2'-amino-2'-deoxyribose, 4'-methyl-2'-deoxyribose, 4'-ethyl-2'-deoxyribose, and 2'-O-methylribose. Modified backbones include phosphorothioate linkages, 5' bridging phosphorothioate linkages, 3'-bridging phosphorothioate linkages, 3'-N-phosphoramidate linkages, methylphosphonate linkages, and boranophosphate linkages.

Additionally, any of these modified bases can be incorporated into the above described nanocircles using conventional methods. For example, if a nanocircle contains a "T", then T-analogs such as 5-fluoro-dU, 5-chloro-dU, and so on could be incorporated in its place. Similarly, C-analogs can be incorporated in place of C in nanocircles.

In Vivo Telomere Extension Applications

Nucleic acid nanocircles can be used in methods to extend the length of a telomere in vivo. The methods can comprise selecting a cell comprising a telomere; and contacting the cell with a nucleic acid nanocircle under conditions suitable for uptake of the nanocircle by the cell. The length of the telomere after uptake of the nanocircle is greater than the length of the telomere before uptake of the nanocircle. The difference in length is preferably at least about 96 nucleotides. The difference can be at least about 1000, at least about 5000, at least about 10000, at least about 15000, at least about 20000, or at least about 25000 nucleotides. The cell can generally be any type of cell. The cell can be a mammalian, fish, bird, amphibian, or microorganism cell. For example, the cell can be a human cell, a bone marrow cell, a yeast cell, a horse embryo or embryo cell, a cow embryo or embryo cell, a pig embryo or embryo cell, a human embryo or embryo cell, or a zebrafish embryo or embryo cell. The contacting step can comprise treatment of the cell with the nanocircle alone. Alternatively, the contacting step can comprise contacting the cell with the nanocircle in the presence of a DNA uptake agent. The DNA uptake agent can generally be any chemical or biological agent which accelerates uptake of nucleic acids into the cell. For example, the DNA uptake agent can be calcium phosphate, a lipid, a cation, polyethyleneimine, a cationic lipid, or a polyaminolipid. The contacting step can comprise treating under electroporation conditions, direct injection conditions, or under other conditions which accelerate uptake of nucleic acids into the cell. The uptake of the circle into the cell can be active or passive.

Normal telomeres in cells may be double-stranded for thousands of base pairs, but have an overhanging G-rich strand that may be roughly 100 nucleotides long. When a telomere in a living cell is elongated by a polymerase using a nanocircle template, only the G-rich strand is immediately elongated. This produces a telomere that has a much longer than usual G-rich strand. However, by the time that this cell has completed its first division, the DNA replication machinery makes a complementary C-rich strand that is nearly as long as the elongated G-rich overhang, and the normal state of the telomere structure is restored.

Extended Growth of Non-cancerous Cell Populations in Culture

Nucleic acid nanocircles can be used in methods for culturing non-cancerous cell populations. Contacting the cell populations with the nucleic acid nanocircles can enhance the growth and expansion of the cultured cells. Cell populations which are dividing in the growth medium will expand, providing large quantities of cells for use in biomedical research and tissue engineering. For cell populations which are not dividing or which are dividing slowly, a growth factor can be added to the culture medium to stimulate cell division. The nucleic acid nanocircles can be added in one dose, can be added at various time points in the cell culturing, or can be added continuously throughout cell culturing. Generally any kind of non-cancerous cell population can be used. Examples of cells grown in culture include pancreas cells, liver cells, blood cells, bone marrow cells, fibroblasts, endothelial cells, skin cells, hepatic cells, kidney cells, neural cells, neurons, oligodendrocytes, nerve cells, bone cells, and stem cells.

Treating Macular Degeneration

Nucleic acid nanocircles can be used in methods for treating macular degeneration. The methods can comprise selecting a mammal comprising an eye that is experiencing macular degeneration; and contacting the eye and a nucleic acid nanocircle under conditions suitable for uptake of the nanocircle by the eye. The degree of macular degeneration of the eye after the contacting step can be less than the degree of macular degeneration of the eye before the contacting step. The mammal can generally be any mammal. For example, the mammal can be human, cat, dog, cow, pig, horse, mouse, rat, sheep, rabbit, or goat. The contacting step can comprise contacting the cell with the nanocircle in the presence of a DNA uptake agent. The DNA uptake agent can generally be any chemical or biological agent which accelerates uptake of nucleic acids into the cell. For example, the DNA uptake agent can be calcium phosphate, a lipid, a cation, polyethyleneimine, a cationic lipid, or a polyaminolipid.

Treatment of the Effects of Skin Aging

Nucleic acid nanocircles can be used in methods to treat the effects of skin aging. The methods can comprise selecting a mammal comprising skin that is experiencing the effects of skin aging; and contacting the skin and a nucleic acid nanocircle under conditions suitable for uptake of the nanocircle by the skin. The effects of skin aging after the contacting step can be less than the effects of skin aging before the contacting step. The effects of skin again can include wrinkles and discoloration of the skin. The effects can be measured by any appropriate dermatological standard. The mammal can generally be any mammal. For example, the mammal can be human, cat, dog, cow, pig, horse, mouse, rat, sheep, rabbit, or goat. The contacting step can comprise contacting the cell with the nanocircle alone or in the presence of a DNA uptake agent. The DNA uptake agent can generally be any chemical or biological agent which accelerates uptake of nucleic acids into the cell. For example, the DNA uptake agent can be calcium phosphate, a lipid, a cation, polyethyleneimine, a cationic lipid, a cationic peptide or peptide analog, a polyaminolipid, or dimethylsulfoxide. The DNA uptake agent can be a treatment method such as electroporation/transdermal application, or "biolistic" high speed particle bombardment (e.g. with a "Genegun").

Treating Degeneration of the Liver

Nucleic acid nanocircles can be used in methods to treat degeneration of the liver and its resulting decrease in liver function and activity. The methods can comprise selecting a mammal comprising a liver that is experiencing liver degeneration; and administering to the mammal a nucleic acid nanocircle under conditions suitable for uptake of the nanocircle by the liver. The liver degeneration after the administering step can be less than the liver degeneration before the administering step. The liver activity after the administering step can be greater than the liver degeneration before the administering step. Liver degeneration and activity can be measured by any suitable medical or clinical assay. The mammal can generally be any mammal. For example, the mammal can be human, cat, dog, cow, pig, horse, mouse, rat, sheep, rabbit, or goat. The administering step can be performed by any medically acceptable method. Examples include IV injection, IP injection, IM injection, transdermal administration, oral administration, inhalation, and intranasal administration.

Anti-cancer Applications

Nucleic acid nanocircles can be used in methods to treat cancer. They can be used in in vitro or in vivo applications. The methods can comprise selecting a mammal diagnosed with cancer; and administering to the mammal a nucleic acid nanocircle under conditions suitable for uptake of the nanocircle by cancer cells. The cancer diagnosis after the administering step can be better than the cancer diagnosis before the administering step. The amount of cancer cells in the mammal after the administering step can be lower than the cancer diagnosis before the administering step. The diagnosis and quantitation of cancer in the mammal can be performed by any acceptable medical or clinical assay. The mammal can generally be any mammal. For example, the mammal can be human, cat, dog, cow, pig, horse, mouse, rat, sheep, rabbit, or goat. The administering step can be performed by any medically acceptable method. Examples include IV injection, IP injection, IM injection, transdermal administration, oral administration, inhalation administration, and intranasal administration. The nanocircles used in anti-cancer applications preferably contain two or more repeats of the complement of a telomere repeat sequence in order to bind to the telomere end. The remaining sequence of the nanocircle preferably contains non-telomere sequences or modified telomere sequences. In this manner, the sequences added onto the telomere end will not be natural telomere sequences. Incorporation of non-telomere sequences into a telomere has been found to be fatal to cells. In this manner, contacting cancer cells or cancer tissue with such a nanocircle will lead to the death of the cancer cells or cancer tissue.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of a DNA Nanocircle Encoding Chimeric Telomeric Repeats

Figure 3A:
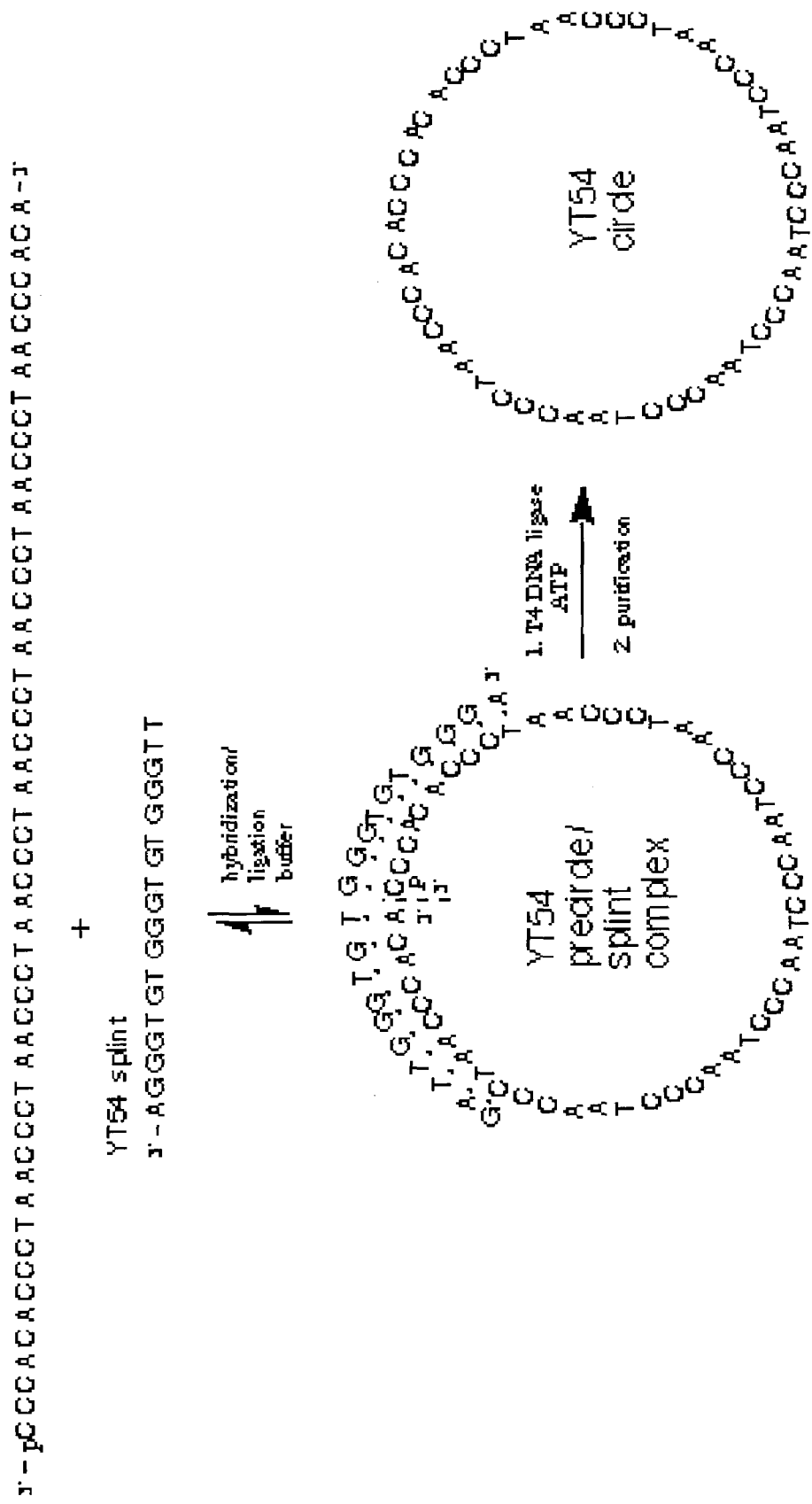
FIG. 3A shows methods for preparing nanocircles with unique ends.

The synthesis of DNA nanocircle templates encoding imperfect telomere repeats (i.e., chimeric or mutated repeats)

is relatively straightforward (see FIG. 3A). A "splint" of nucleic acid, ca. 12-53 nucleotides long, (or a nucleic acid analog known to hybridize to DNA sequences) is designed to be perfectly complementary to the opposite ends so that on binding the linear circle precursor, the 5' and 3' ends of the circle precursor are brought into immediately adjacent positions in a double helix. The precursor DNA contains a 5' phosphate for enzymatic ligation (or a 3' or 5' phosphate for chemical ligation). For closure into circular form, an enzyme such as T4 DNA ligase or Tth DNA ligase is added along with ATP in a buffer sufficient to allow ligation. Alternatively, chemical ligation with agents such as cyanogen bromide, N-cyanoimidazole, EDC, and water soluble carbodiimides can be performed. Note that modified bases are also contemplated for the splint oligonucleotide, and may assist in the proper hybridization.

Example 2

Preparation of the YT54 DNA Nanocircle

The linear precursor had the sequence 5'-pdCCC ACA CCC TAA CCC TAA CCC TAA CCC TAA CCC TAA CCC TAA CCC TAA CCC ACA-3' (SEQ ID NO:18), and the splint had the sequence 5'-dAGG GTG TGG GTG TGG GTT AG-3' (SEQ ID NO:19). The ligation reaction was carried out in 50 mM Tris-buffer (pH 7.5) that contained 1 µM linear precircle, 1.2 µM template strand, 10 mM $MgCl_2$, 5 µM ATP, 10 mM DTT, and 0.34 units/µL T4 DNA Ligase. The reaction was incubated at room temperature for 18 hours. The mixture was then dialyzed against distilled water and lyophilized. Preparative purification of circular product (see FIG. 3A) was carried out using denaturing 20% polyacrylamide gels.

Example 3

Preparation of DNA Nanocircle Encoding Perfect Homogeneous Repeats

The preparation of nanocircles encoding perfect homogeneous repeats all the way around the sequence is considerably more difficult, and required new methods to solve the problem. The reason for the difficulty is that a splint DNA molecule will preferentially bind the middle of the circle precursor rather than the two ends. Thus cyclization by ligase enzymes or chemical methods is prevented.

An initial approach to solving this problem failed. The use of different protecting groups on the ends versus the middle of the precursor was envisioned. First, the end protecting groups would be removed, allowing the splint to bind only at the ends by preventing effective binding at the middle. At the ends of the DNA, rapid deprotection chemistry such as PAC protecting groups (rapid-deprotecting phosphoramidites were purchased from Glen Research) were used. Benzoyl protecting groups on the adenines in the HT54 nanocircle precursor were used in the middle of the sequence; these were not deprotected under mild conditions and thus were expected to prevent binding of the splint. However, results showed that although the benzoyl protecting groups did remain, surprisingly they did not prevent binding of the splint. Little or no HT54 nanocircle was formed by T4 DNA ligase using this approach.

Figure 3B:
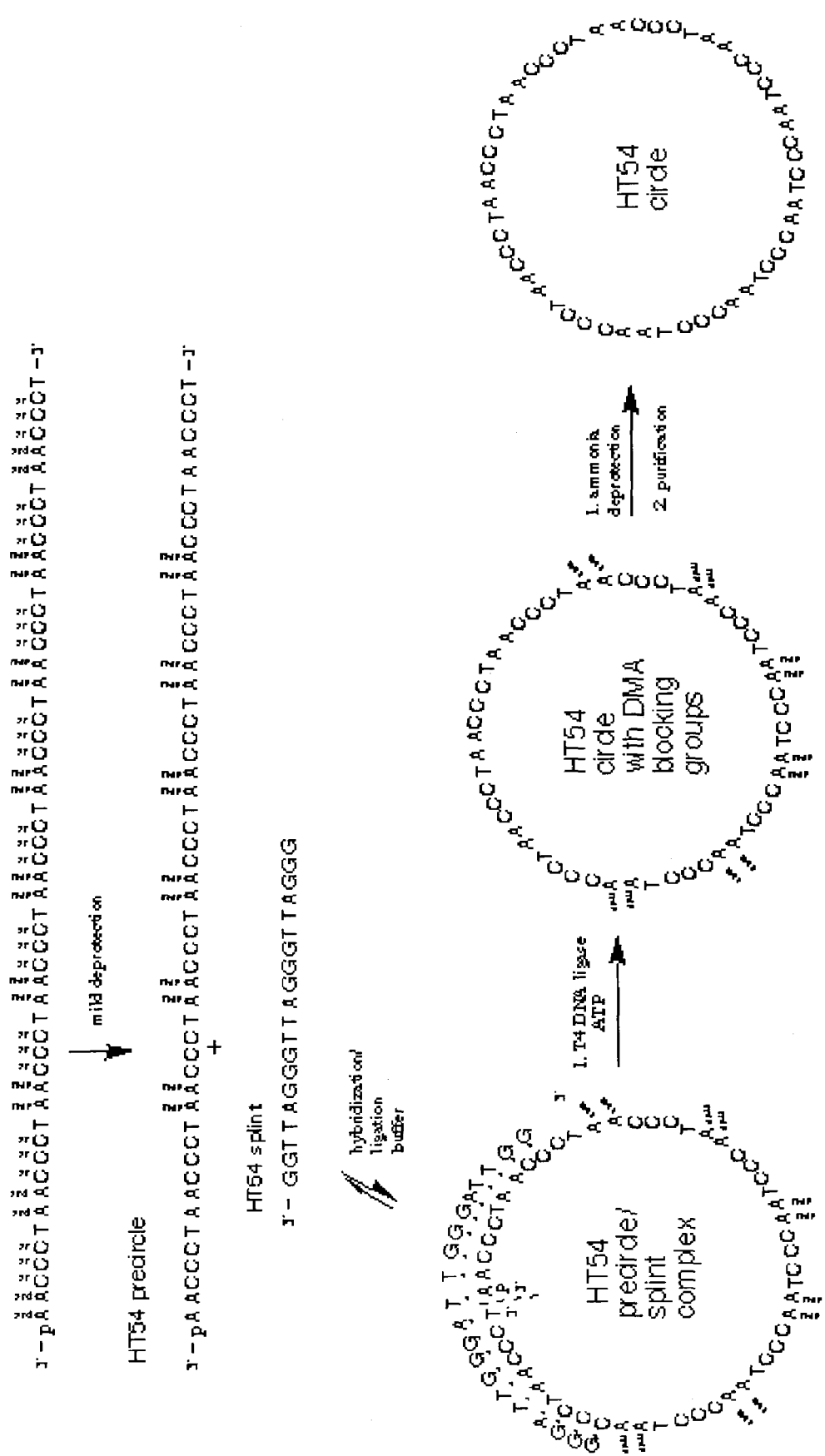
FIG. 3B shows methods for preparing nanocircles with homogeneous repeating sequences.

A different chemical approach using the DMA (dimethylacetamidine) protecting group on adenines in the middle of the precursor was attempted (see FIG. 3B). The DMA protecting group was expected to be "orthogonal" to the rapid-deprotecting groups such as PAC, meaning that the PAC groups could be removed without removing the DMA groups (see FIG. 2). This approach was described in Lindstrom, U. and Kool, E. T., *Nucleic Acids Res.* 30: e101; 2002. In this second approach, ultra-mild chemistry (Glen Research) for the ends of the DNA was again used. Once the crude protected HT54 linear DNA was synthesized containing these protecting groups, we first treated with mild deprotection chemistry to remove the groups. We then used the splint and T4 DNA ligase and ATP to close the circle in high yield. Finally, stronger deprotection was used to remove the remaining DMA protecting groups. This resulted in the perfect HT54 nanocircle, which was purified by gel electrophoresis.

Example 4

Preparation of HT54 DNA Nanocircle

DNA oligonucleotides were synthesized on an Applied Biosystems 392 synthesizer using β-cyanoethylphosphoramidite chemistry. Ultra-mild deprotection phosphoramidites were purchased from Glen Research. No changes to the standard protocol were needed for the couplings of dimethylacetamidine-dA phosphoramidite. 5'-phosphorylation was carried out with Phosphate-ON phosphoramidite reagent (Glen Research). The sequence synthesized was 5'-d(pacApacAC CCT pacApacAC CCT dmaAdmaAC CCT dmaAdmaAC CCT dmaAdmaAC CCT dmaAdmaAC CCT dmaAdmaAC CCT dmaAdmaAC CCT pacApacAC CCT)-3' (SEQ ID NO:14), where pacA denotes the mild/rapid deprotecting version of A, and dmaA represents dimethylacetamidine-protected A, which remained on the DNA until the second deprotection. All Cs were protected as N4-acetyl derivatives. Deprotection was done with 0.05M $K_2CO_3$/MeOH for 4-12 hours at room temperature for the ultra-mild deprotection bases (a minimum of 8 hours is needed when 5'-phosphorylation reagent is used). For the dma-dA base, cleavage was achieved with either $NH_4OH$ for 8 hours at 55° C. or with AMA ($NH_4OH$/$MeNH_2$ (40% in water) 1:1) for at least 8 hours at room temperature. Room temperature is preferred for circular DNA. Cleavage of the oligomer from the support was simultaneously accomplished under all of these conditions.

Oligomers were purified by preparative 20% denaturing polyacrylamide gel electrophoresis and quantitated by absorbance at 260 nm. Molar extinction coefficients for the oligonucleotides were calculated using the nearest neighbor method. Ligations of linear 5'-phosphorylated DNAs were carried out by the method previously described for cyclization of DNA using an 18mer DNA template (5'-GTTAGGGT-TAGGGTTAGG-3'; SEQ ID NO:15) to align the reactive ends and T4 DNA Ligase (New England Biolabs) to achieve the ligation. The reactions were typically carried out in 50 mM Tris-buffer (pH 7.5) that contained 1 µM linear precircle, 1.2 µM template strand, 10 mM $MgCl_2$, 5 µM ATP, 10 mM DTT, and 0.34 units/µL T4 DNA Ligase. One doubling of DNA-concentrations could be done without affecting the yield. Reactions were incubated at room temperature for 18 hours. The mixtures were then dialyzed against distilled water and lyophilized. Preparative purification of circular products was carried out using denaturing 20% polyacrylamide gels. Circular DNA was detected as a significantly slower moving band by UV-shadowing. Analytical gels were visualized with Stains-All dye (Sigma). Isolation of DNA was accomplished by crushing the gel and extracting with 0.2M NaCl for 12 hours. Conversion of precircle to circle often appeared high by UV-shadowing, but isolated yields based on linear precursor were usually less than 30%. Oligonucleotides were obtained as the sodium salt after dialysis and yields of the purified circular products were determined by UV absorbance at 260 nm.

Example 5

Analysis Of HT54 DNA Nanocircle

Confirmation of circularity was provided by nicking with S1 endonuclease; initial cleavage of a circle produced a single band with the mobility of the full-length linear precursor. Products of cleavage were best analyzed by 20% denaturing PAGE. The following reactions were performed to confirm the feasibility of using "orthogonal" protecting groups in preparing nucleic acid nanocircles. The spectroscopic data was as follows.

d(acC ipr-pacG dmaA T)-CPG (SEQ ID NO:9)→d(CAGAT) (SEQ ID NO:7) [NH$_4$OH/MeNH$_2$ (40% in water) 1:1, 12 h, rt]: MALDI-TOF-MS calcd for C$_{49}$H$_{63}$N$_{20}$O$_{27}$P$_4$ (M+H): 1488.03. Found: 1490.76. These conditions caused complete deprotection of the DNA.

d(acC pacA ipr-pacG dmaA T)-CPG (SEQ ID NO:9)→d(C A G dmaA T) (SEQ ID NO:10) [K$_2$CO$_3$/MeOH 12 h, rt]: MALDI-TOF-MS calcd for C$_{53}$H$_{70}$N$_{21}$O$_{27}$P$_4$ (M+H): 1557.14. Found: 1559.52. These conditions effected removal of the pac, ipr-pac, and acetyl protecting groups, but not the dma protecting group.

d(C A G dmaA T) (SEQ ID NO:10)→d(CAGAT) (SEQ ID NO:7) [NH$_4$OH, 8 h, 55° C.]: MALDI-TOF-MS calcd for C$_{49}$H$_{63}$N$_{20}$O$_{27}$P$_4$ (M+H): 1488.03. Found: 1488.57. These conditions effected removal of the dma protecting group.

d(C A G dmaA T) (SEQ ID NO:10)→d(CAGAT) (SEQ ID NO:7) [NH$_4$OH/MeNH$_2$ (40% in water) 1:1, 8 h, rt]: MALDI-TOF-MS calcd for C$_{49}$H$_{63}$N$_{20}$O$_{27}$P$_4$ (M+H): 1488.03. Found: 1489.51. These conditions effected removal of the dma protecting group.

Example 6

Use of mC Nucleotides to Improve Hybridization Properties 5-methyl-CTP or 5-methyl-dCTP can be used to create a nucleic acid nanocircle that displays stronger hybridizing properties than the corresponding nucleic acid nanocircle made using CTP or dCTP. An example of such a nanocircle is MHT54 (circular d(mCmCmCTAA)$_9$; SEQ ID NO:38) encoding the complement of the human telomere repeat sequence. Nanocircle MHT54 can be prepared using the MHT54 precircle (SEQ ID NO:24) and MHT54 splint (SEQ ID NO:25) under the conditions described above.

Example 7

Elongation of Telomeric Primers in Vitro with Nanocircles HT54 and/or YT54

Experiments showed that standard telomere-like primers could be efficiently elongated by many or most common DNA polymerases when a nanocircle template was provided. Products were as much as several to many thousands of nucleotides in length, starting with a simple 18 nucleotide primer having the same sequence as the ends of human telomeres. By contrast, linear control templates of the same length and sequence were not efficient templates for extension of this primer, giving products generally 100 nucleotides or less in length.

All extension reactions contained 100 nM HT54 nanocircle, 100 µM 18mer primer (5'-TTAGGGTTAGGGT-TAGGG-3'; SEQ ID NO:11), and 1 mM each of dATP, dCTP, dGTP, and dTTP in a total reaction volume of 25 µl. For DNA polymerase α (Chimerx), reactions contained 60 mM Tris-HCl (pH 8.0), 5 mM MgCl$_2$, 0.3 mg/ml BSA, 1 mM DTT, 0.1 mM spermidine, and 0.15 units/ml polymerase α. Reactions using DNA polymerase β (Chimerx) contained 50 mM Tris-HCl (pH 8.7), 5 mM MgCl$_2$, 100 mM KCl, 0.4 mg/ml BSA, 1 mM DTT, and 0.16 units/µl polymerase β. Reactions using genetically modified exonuclease free Klenow Fragment (KF$^-$) of DNA polymerase I (United States Biochemical) contained 50 mM Tris-HCl (pH 7.5), 10 mM MgCl$_2$, 1 mM DTT, 50 µg/ml BSA, and 0.4 units/µl KF$^-$. For Sequenase 2.0 (exonuclease free T7 DNA polymerase, United States Biochemical), reactions contained 40 mM Tris-HCl (pH 7.5), 20 mM MgCl$_2$, 0.2 mM DTT, and 0.52 units/µl. Reactions using the thermophilic Deep Vent DNA polymerase (New England Biolabs) contained 10 mM KCl, 10 mM (NH$_4$)$_2$SO$_4$, 20 mM Tris-HCl (pH 8.8), 2.0 mM MgSO$_4$, 0.1% Triton X-100, and 0.08 units/ml Deep Vent. The Deep Vent reactions were incubated at 70° C. whereas all other extension reactions were carried out at 37° C. All reactions proceeded for 4 hours and were stopped by addition of an equal volume of PAGE loading buffer (10 mM EDTA in formamide). Reaction mixtures were then run on 20% denaturing PAGE gels at 30 W for 2 hours.

Example 8

Use of Other Polymerases for Nanocircle Extension

In separate reactions, nanocircle HT54 (circular template) is incubated a telomere-like primer and with DNA polymerases α, β, γ, or δ from either human or yeast sequences or isolated from human or yeast cells. Also present in the mixtures are at least two of the four natural deoxyribonucleotides (dATP, dGTP, dCTP, dTTP) at 1 µM to 5 µM concentration each, and salts and buffers sufficient for activity. The selection of how many deoxyribonucleotides to use depends on the bases in the nanocircle sequence. Assays can be performed to show that these enzymes are also able to extend telomere-like primers efficiently in vitro, affording extended single-stranded telomeres of length 500 nucleotides and longer, whereas linear control templates do not act as efficient templates, giving products mostly less than 100 nucleotides in length. Assays can also be performed to show that other nanocircles encoding the same telomere repeat, such as HT72, can also extend primers efficiently to make telomeres.

Example 9

Sequencing of Produced Telomeres

Telomeres synthesized by nanocircles were confirmed by the use of standard Sanger sequencing methods. Nanocircles encoding completely naturally occurring sequences produced natural telomeres. When nanocircles encoding chimeric sequences or mutated telomere sequences are used, the Sanger sequencing confirms the presence of the predicted repeating sequences encoded by the rolling circle.

Example 10

Positive TRAP Assay of Nucleic Acid Nanocircles Producing Telomeres

The TRAP assay is a standard measure of telomerase activity. Solutions containing telomerase and at least two of the four deoxynucleotides gave a positive TRAP assay result, showing extended bands indicative that telomerase extended the telomere-like primer. DNA nanocircles also gave a positive TRAP assay result in the presence of DNA polymerase enzymes using the same primer and the same four natural nucleotides.

Example 11

Expansion of CD34$^+$ Bone Marrow Cells by HT54 Nanocircle

Allogeneic bone marrow transplants are commonly used for treatment of leukemias. If long-term growth and expansion of a population of CD34$^+$ bone marrow cells and their progeny were possible, then the need for taking multiple bone marrow samples from donors would be lowered significantly. Long-term growth and expansion of bone marrow cells would generally be useful both for treatment of blood diseases and for blood research.

A sample of CD34$^+$ bone marrow cells can be treated with HT54 nanocircle at concentrations and times that allow telomeres to be elongated. The treatment can be performed either with naked DNA alone, or with known DNA uptake reagents. Continued passaging of cells can be done to increase the population, and the dosing of the cells with the HT54 nanocircle is repeated as needed to keep the population from entering senescence due to shortened telomeres. If desired, known growth factors can be added to increase the rate at which the population grows. Other known human-repeat nanocircles, such as HT72, can also be shown to be effective.

Example 12

Extension of Telomeres in a Breast Epithelial Cell Line and in Primary Breast Epithelial Tissues Expansion and long-term growth of epithelial tissue would be important for tissue engineering and for biomedical research. Primary epithelial tissue can in principle be used in growing skin for treatment of bum victims and for growing new blood vessels, for example. Such tissue cultures can be grown much longer (perhaps indefinitely) and in much larger quantities by dosing with nanocircles such as HT54 to elongate telomeres.

A sample of breast epithelial cells can be treated with HT54 nanocircle at concentrations and times that allow telomeres to be elongated. The treatment can be performed with either naked DNA alone, or together with known DNA uptake reagents. Continued passaging of cells can be done to increase the population, and the dosing of the cells with the HT54 nanocircle is repeated as needed to keep the population from entering senescence due to shortened telomeres. If desired, known growth factors can be added to increase the rate at which the population grows. Other known human-repeat nanocircles, such as HT72, can also be shown to be effective.

Example 13

Extension of Telomeres in Yeast (*Saccharomyces cerevisiae*)

The yeast *Saccharomyces cerevisiae* is an important model organism for study of telomere biochemistry and biology. Nanocircles can be used in yeast to extend telomeres with natural yeast sequences or with mutations or chimeric sequences. This makes nanocircles especially useful as research tools. Chimeric telomere sequences can be made with circles encoding some yeast repeats and some repeats from another organism. The circle YT54 is one example. Virtually any other repeating sequence could be made using the rolling circle approach, by encoding the sequence into a nanocircle. The only requirement for successful elongation is that the nanocircle contain at least six consecutive nucleotides (and preferably at least ten) that are perfectly complementary to the telomere end.

Example 14

Therapeutic Treatment of Cellular Senescence

A number of human disease states are known to involve cellular senescence. Localized treatment of aging cell populations with telomere encoding nanocircles is intended to renew the cells' ability to divide and grow, by delaying the onset of senescence.

Macular degeneration in the eye is associated with cellular senescence and shortened telomeres. A perfect human-repeat nanocircle such as HT54 can be used to treat the eye locally to renew the local cellular population. It can be used either alone or in combination with growth factors that will help the cells divide. The nanocircle can be used either as naked DNA or in combination with a known DNA uptake or delivery reagent. It can be administered to the affected eye either by injection or by topical treatment. Examination of the eye after a course of treatment shows lessened macular degeneration and evidence of new cell growth.

Skin aging (with associated wrinkling, loss of elasticity and dryness) is associated with cells becoming senescent with shortened telomeres. A perfect human-repeat nanocircle such as HT54 can be used to treat the skin locally to renew the local cellular population. It can be used either alone or in conjunction with growth factors that will help the cells divide. The nanocircle can be used either as naked DNA or is combined with known DNA uptake or delivery reagents. It can be administered to the affected skin either by injection or by topical treatment in a cream that aids skin absorption. Examination of the skin after a course of treatment shows lessened signs of aging and senescence and evidence of new cell growth.

Degenerative diseases of the liver, such as those caused by alcoholism or by viral hepatitis, are associated with liver cells entering senescence and with shortened telomeres. A perfect human-repeat nanocircle such as HT54 can be used to treat the liver either locally or systemically to renew the local cellular population. It can be used either alone or in conjunction with growth factors that will help the cells divide. The nanocircle can be used either as naked DNA or in combination with known DNA uptake or delivery reagents. It can be administered to the liver either by local treatment with surgery or by systemic treatment (such as intravenously) in combination with molecules or preparations (such as liposomes) that promote localization of the DNA to the liver. Examination of the liver after a course of treatment shows lessened signs of aging and senescence and evidence of new cell growth.

Example 15

Therapeutic Treatment of Cancer and Cancer Cells

Therapeutic treatment of cancer in humans and in human cells can be achieved by the use of mutant telomere-encoding nanocircles. Recent studies have shown that human cancer cells can be killed by engineering mutant sequences into their telomeres. It has been reported (Kim, M. M., et al., *Proc. Natl. Acad. Sci. U.S.A.* 98: 7982-7987, 2001) that adding new telomeric DNA with non-natural sequences results in apoptosis of the cells.

The use of nanocircles encoding mutant telomere sequences can be used to kill cancer cells. If a human is treated systemically by mutant telomere-encoding nanocircles (MTENs), these molecules are expected to be generally cytotoxic (as are many anticancer agents). Systemic treatment by injection is expected to kill cancer cells more efficiently than normal cells because the cancer cells are dividing more rapidly and are undergoing more rapid metabolism. Thus, treatment of a cancer patient with a chemotherapy including MTENs can result in improved long-term prognosis. Alternatively, during tumor-removal surgery, the margins of the tissue surrounding the excised tumor are treated with MTENs to kill any remaining cancerous cells. Finally, systemic treatment of cancer patients can be done by administering MTENs with agents or molecules (such as antibodies) that tend to localize MTENs to tumors.

Lastly, MTENs can be used to treat cellular populations ex vivo. For example, autologous bone marrow samples from a leukemia patient are treated with MTENs to selectively kill any remaining cancerous cells before the healthy cells are reimplanted back into the patient.

Example 16

Extension of Telomeres in Zebrafish (*Danio rerio*) Embryos

Telomere-encoding nanocircles (TENs) can be used to treat whole organisms or embryos to extend telomeres for research purposes or to increase organismal lifespan. Fertilized, viable zebrafish embryos can be treated with TENs such as HT54 to elongate telomeres in all the cells of the embryo. The fish so treated can be observed to have elongated telomeres by in situ hybridization. They can be observed to develop normally, but to have cell populations with increased lifespan. Embryos from other organisms, such as mammals, can have a similar outcome after treatment with TENs.

Example 17

Extension of Telomeres in Human Artificial Chromosomes

Human artificial chromosomes (HACs) have been shown to be a potentially useful way to genetically modify human cells in a stable way. HACs must contain centromeres and telomeres in order to be viable. Current methods for placing telomeres on HACS, using cloned telomeric sequences less than 5 kb in length, make HACs with telomeres that are considerably shorter than telomeres in stably dividing normal human cells. The presence of short-telomere HACs in cells can lead to a tendency to become senescent and undergo apoptosis.

TENs can be used to construct telomeres in HACs that are much longer, approximating natural telomeres. A human artificial chromosome under construction can be treated with a TEN such as HT54 in the presence of a commercially available DNA polymerase such as T7 DNA polymerase and the four natural nucleotides (dNTPs) in a buffer that supports polymerase activity. This can result in extension of the telomere G-rich strand by up to thousands of nucleotides. The resulting HAC is more effective in stable genetic engineering of the cells, as there is no shortened telomere signal that tends to make the cell enter senescence.

Example 18

Extension of Artificial Telomeres for Detection of DNAs, RNAs, and Proteins

There are several methods currently available commercially for detection and identification of telomeres. Examples include the TRF assay, long highly fluorescent telomere fluorescence in situ hybridization (FISH) probes, and short fluorescent telomere hybridization probes constructed from DNA or PNA. The methods are sensitive and specific for human telomeric repeats.

Modified telomere-encoding nanocircles can be used to produce "artificial telomeres" on natural RNA or DNA molecules. These artificial telomeres can be detected sensitively and selectively by existing telomere detection/identification methods.

A modified TEN can be synthesized that encodes natural human telomere repeats, and also contains a segment 6-22 nucleotides long that is complementary to the 3' end of an analyte DNA or RNA that is to be detected. The solution containing the analyte DNA or RNA can be incubated with the modified TEN, a DNA polymerase such as Klenow polymerase or T7 DNA polymerase, and the four natural nucleotides (dNTPs) at concentrations and in a buffer that support polymerase activity. This results in extension of the 3' end of the analyte RNA or DNA with a repeating normal human telomere sequence (interspersed with the segment complementary to the analyte end). This can be detected by TRAP assay, by long fluorescent FISH probes, or by labeled oligonucleotide probes or PNA probes that are known to detect human telomeres. The method can be done with multiple modified TENs simultaneously to detect multiple RNAs or DNAs simultaneously. Any of several DNA polymerases are found to efficiently extend telomeres on DNA analytes. For RNA analytes, the most active and successful DNA polymerases are those that are already known to be active with RNA primers, such as Klenow polymerase.

Similarly, a telomeric primer can be attached to an antibody using conventional methods. The antibody can be used in immunoassays such as dot blots, Western blots, and ELISAs to detect the presence of a protein or other immunogenic material. A nanocircle can be used to generate an artificial telomere attached to the antibody-antigen complex. The telomeric primer can alternatively be attached to biotin, digoxigenin, or other recognizable "tag" molecules.

Example 19

Extension of Telomeres on Surfaces for Trapping/Immobilizing Chromosomes

It is useful to trap segments of chromosomes, or whole chromosomes, on solid supports such as surfaces, microarrays on plastic or glass, or on plastic or glass beads. This can be accomplished by immobilizing a known telomere primer on the solid support using known methods. The 3' end is free for enzymatic extension. The oligonucleotide can be placed on the solid support either by synthesizing it there, by reacting its 5' end with the support after the primer has been synthesized, or by noncovalently associating the 5' end with the support.

The primer on the support can be extended with natural telomeric sequences using a TEN. This can be done by contacting the primer on the support with a DNA polymerase such as T7 DNA polymerase, and the four natural nucleotides (dNTPs) at concentrations and in a buffer that support polymerase activity. For example, if the primer 5'-d(TTAGGG)$_3$ (SEQ ID NO:60) is associated with the support, then the nanocircle HT54 (SEQ ID NO:30) will extend it to a length of hundreds or thousands of nucleotides. If a solution containing chromosomes or chromosome fragments is washed over this surface in hybridization buffer, then the chromosomes or fragments containing complementary telomeric sequences will be non-covalently bonded to the support. Washing can remove undesired noncomplementary sequences of DNA or RNA.

Alternatively, the C-rich strand can be extended on the surface. This traps the G-rich strand of telomeres on chromosomes or fragments. An example of a C-rich primer that can be used for this is 5'-d(CCCTAA)$_3$ (SEQ ID NO:61), and an example of a TEN that can successfully extend this is circular d(TTAGGG)$_n$ (SEQ ID NO:1).

Example 20

Synthesis of Telomeres to be Used as Telomere Probes

TENs are especially useful in preparation of long repeating DNAs that are complementary to telomeres. By incorporation of detectable molecules during synthesis, this is a useful method for preparing probes for telomeres that can allow telomeres to be detected by hybridization. Examples of detectable molecules include 5-BrdUTP, which can be incorporated in place of dTTP, or a fluorescent conjugate of dUTP, or a biotin or digoxigenin conjugate of dUTP. These are all commercially available. If one desires a C-rich probe that detects the G-rich strand of telomeres, then one can use a primer such as 5'-d(CCCTAA)$_3$ (SEQ ID NO:61), and a TEN that can successfully extend this, such as circular d(TTAGGG)$_9$ (SEQ ID NO:62). If one desires a G-rich probe that detects the C-rich strand of telomeres, then one can use a primer such as 5'-d(TTAGGG)$_3$ (SEQ ID NO:60), and a TEN that can successfully extend this, such as HT54 (SEQ ID NO:30).

Example 21

Telomere Extension in HEK 293 Cells

HEK 293 cells are an immortalized tumor-derived cell line, originating from human embryonic kidney cells. Cultures of 293 cells plated at 20-30% confluence were incubated with the following reaction mixtures: 1) 50 μL OptiMEM serum-free medium containing 1 μM HT54 circle and 0.6 μL Oligofectamine 2) a similar solution, containing 3.5 μM circle and no Oligofectamine and 3) a control mixture containing only OptiMEM medium. The incubation proceeded for 4 hours at 37° C., after which the cultures were supplemented with fetal bovine serum (final concentration 10%) and grown until they contained approximately $10^6$ cells (approximately 2 days). The cultures were arrested in metaphase by addition of colcemid and fixed in a 1:3 acetic acid/methanol mixture.

Metaphase slides prepared from these suspensions were analyzed by quantitative fluorescence in situ hybridization. The slides were pretreated by fixation in 3.7% formaldehyde and dehydrated with ethanol (2 minutes each in 70%, 85%, 95% ethanol). After drying, they were incubated with a solution containing 3 μg/mL fluorescein-labeled peptide nucleic acid probe with the sequence (CCCTAA)$_3$ (SEQ ID NO:61). This hybridization was done for 4 minutes at 86° C., followed by 1 hour at room temperature. Unbound probe was washed away (phosphate-buffered saline/0.1% Tween-20 detergent, 5 minutes at 65° C.), and the slides were dehydrated again with ethanol.

Figure 4:
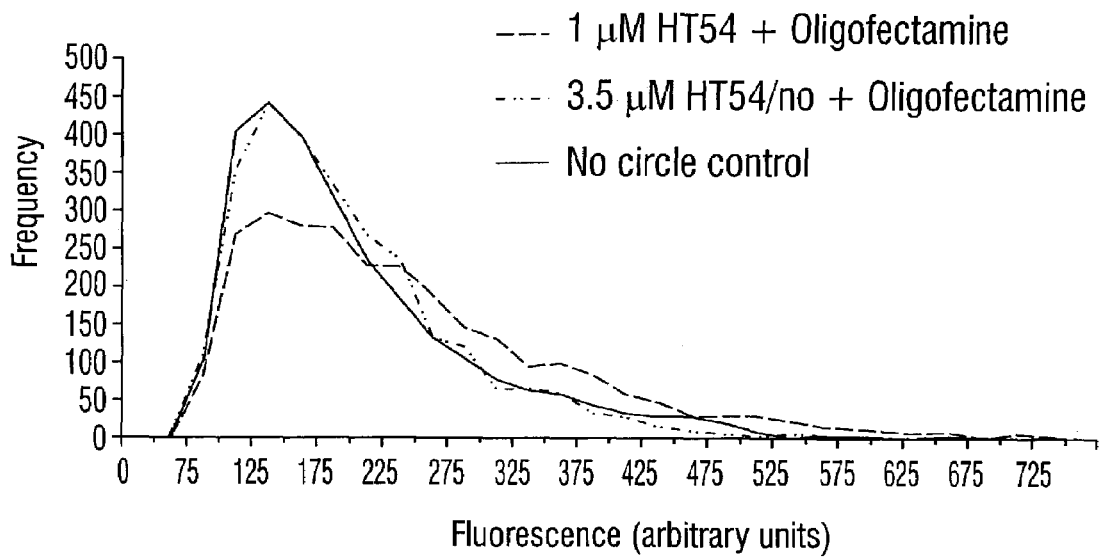
FIG. 4 shows the integrated fluorescence intensity distribution of telomere extension in HEK 293 cells.

After counterstaining with DAPI, slides were visualized with an epifluorescence microscope. Images were captured with a digital camera and the integrated fluorescence intensities of the telomeric signals were measured using the software program TFL-TELO. FIG. 4 show the frequency distribution of the intensities. Approximately 2000 telomeres from ca.15 metaphases were measured for each slide. Because there were slightly different numbers of data points for each slide, the distribution was normalized based on the total number of data points. Calculations from the Figure are shown in the following table.

|  | 1 μM circle | 3.5 μM circle | No circle |
|---|---|---|---|
| Mean | 219.272913 | 172.400866 | 176.46672 |
| Standard Error | 2.36730524 | 1.89780224 | 2.15264151 |
| Median | 190.21 | 152.27 | 149.91 |
| Mode | 261 | 217 | 206 |
| Standard Deviation | 122.803603 | 83.0925353 | 93.2121118 |
| Sample Variance | 15080.7249 | 6904.36943 | 8688.49779 |
| Kurtosis | 2.63478485 | 2.5926724 | 3.50771671 |
| Skewness | 1.4058209 | 1.39514159 | 1.56377658 |
| Range | 878.15 | 585.75 | 810.71 |
| Minimum | 60 | 60 | 60 |
| Maximum | 938.15 | 645.75 | 870.71 |
| Sum | 590063.41 | 330492.46 | 330875.1 |
| Count | 2691 | 1917 | 1875 |
| Confidence Level (95.0%) | 4.64192537 | 3.72197457 | 4.22182475 |

This experiment shows evidence that the DNA circle HT54 caused telomeres to become elongated with this single treatment in the presence of Oligofectamine to aid uptake. The data show that the HT54+Oligofectamine treatment yielded a greater median telomere signal (190 versus 145) relative to the control. The shape of the plots (note esp. the dark blue and yellow lines in the figure) suggests that telomeres near the average length (the maximum in the plots near 130 arb. fluorescence units) were elongated, which resulted in a drop in the number of signals at average length, and a corresponding increase in the numbers at longer lengths (between 250 and 550 arb. units). Making the reasonable assumption that fluorescence signal correlates linearly with telomere length, one can estimate that the average-length telomeres that were successfully extended, were extended to as much as two to three times their original length. If the original telomere length averages 5 kB (which is common in tumor-derived cell lines), then some of the telomeres were extended to 10-15 kB, close to the average telomere length in new primary cells (roughly 10-15 kB).

Example 22

Uptake of Fluorescein-labeled 54mer Oligonucleotide in KG1a Cells

KG1a (ATCC CCL-246.1) cells are obtained from bone marrow tissue with acute myelogenous leukemia. Kg1a cells (ATCC CCL-246.1) were grown in 10% FBS/RPMI medium. One hour before transfection, cells were washed and plated in RPMI (600 μl) at $1.6 \times 10^6$ cells/well in a 6-well plate. For each well, DNA (2-16 nmol of HT54) was diluted in RPMI (180 μl), mixed with Lipofectamine (20 μl) and incubated at room temperature for 30 minutes. The DNA-Lipofectamine mixture was added to the cell cultures and cells were incubated at 37° C. After 4 hours, 20% FBS/RPMI medium (800 μl) was added to each well and cells were then transferred to a 96-well plate (200 μl/well). For each DNA concentration tested 8 wells were used. Cells were analyzed by flow-FISH (flow cytometric analysis of fluorescence in situ hybridization), 24 and 48 hours after transfection.

Figure 5:
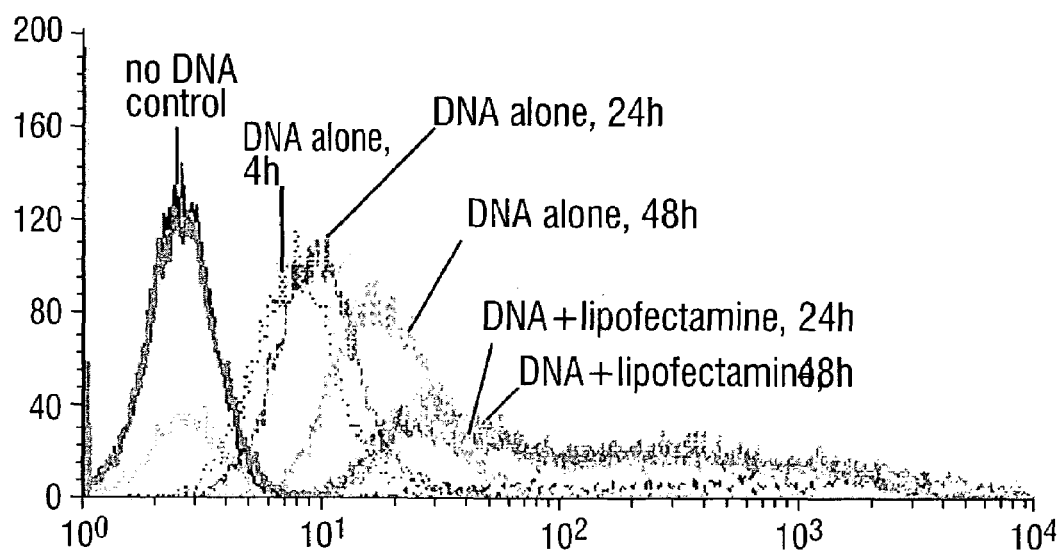
FIG. 5 shows the fluorescence of cells treated with fluorescein-labeled 54mer oligonucleotide.

Kg1a cells growing in 10% FBS/RPMI were transferred to a 6-well plate ($1 \times 10^6$ cells/ml, 1.6 ml/well). Different amounts of HT54 DNA were added to each well (2-16 nmol/well) and cells were transferred to a 96-well plate (200 μl/well) and incubated at 37° C. Again, for each DNA concentration 8 wells were used. Cells were analyzed 24 and 48 hours after transfection. Fluorescence (the abscissa) is plotted versus cell counts (the ordinate); see FIG. 5.

The data show that 54mer DNAs complementary to telomere sequences appear to be taken up into the cells (or are at least associated with them). There is a time-dependent uptake, with increases generally seen from 4 to 24 to 48 hours, although the majority of the signal is seen by 24 hours. Treatment with DNA alone ("naked" DNA) gives a clear time-dependent signal, and adding Lipofectamine clearly increases the average signal (and thus uptake), but it also greatly broadens the distribution of signal. This suggests that Lipofectamine increases the uptake but does so with widely varying efficacy in different cells. Overall the data suggests that either method can allow for DNA uptake (or association) in or with cells.

Example 23

Telomere Extension in KG1a Cells

Cell cultures were analyzed by flow-FISH following the method developed by Lansdorp (G. M. Baerlocher et al, Cytometry 47: 89-99, 2002) with a few modifications. Briefly, cells from 1 or 2 wells per DNA concentration, treated as in Example 22, were transferred to a 1.5 centrifuge tubes and washed with phosphate buffered saline (PBS). Cells were resuspended in 300 ml of hybridization mixture (70% deionized formamide, 20 mM Tris pH: 7.4, 1% BSA) with either no probe or with 0.3 μg/ml telomere-PNA probe. After 20 minutes at room temperature, cells were heated at 80° C. for 15 minutes in a heat block and then left in the dark at room temperature for 90 minutes. After hybridization, the cells were washed with a wash solution (70% formamide, 10 mM Tris, 0.1% BSA, and 0.1% Tween 20) at room temperature ($3 \times 1$ ml). Cells were resuspended in 250 μl of PBS for flow cytometry analysis. No DNA counterstain was used in these experiments.

Telomere fluorescence was measured on a FACSCalibur (Becton Dickinson) and data was analyzed using Cell Quest (Becton Dickinson) or FlowJo (Tree Star). Control experiments included untreated cells with and without PNA probe.

Figure 6A:
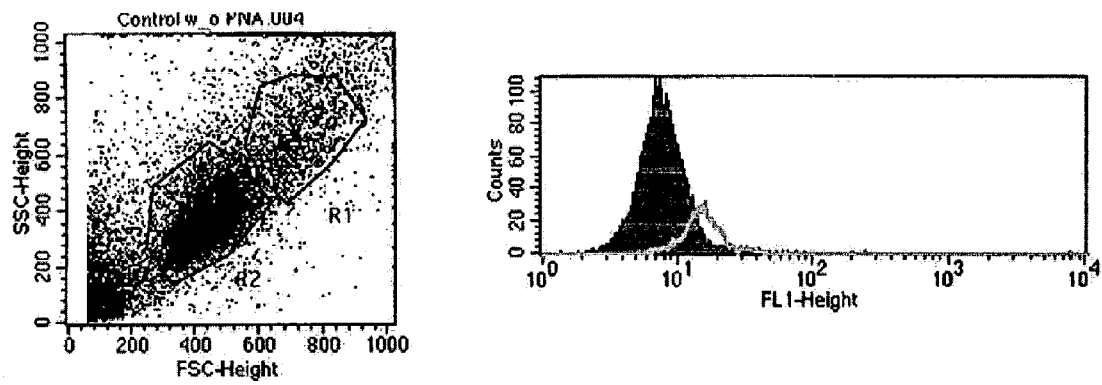
FIG. 6A is for control samples without PNA, 6B is for untreated cells with PNA telomere probe, and 6C is for cells treated with 2 µM circle.
Figure 6B:
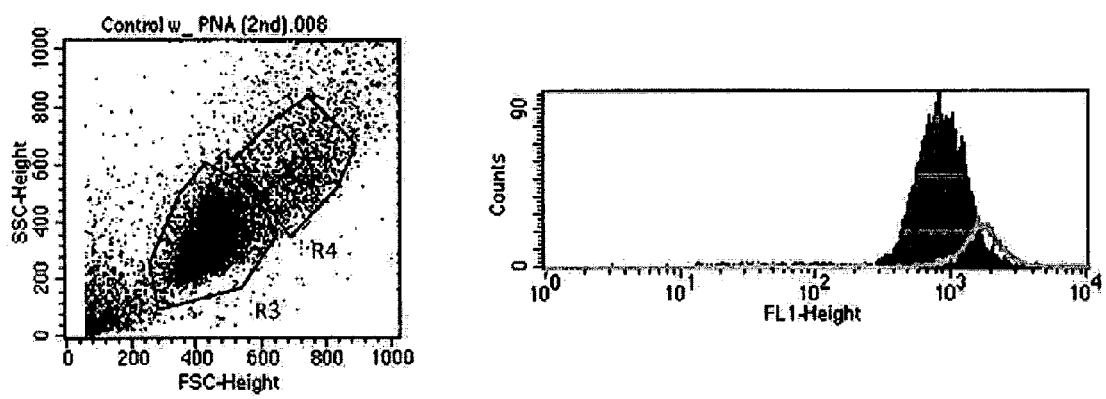
FIG. 6 shows flow-FISH results for telomere fluorescence.
Figure 6C:
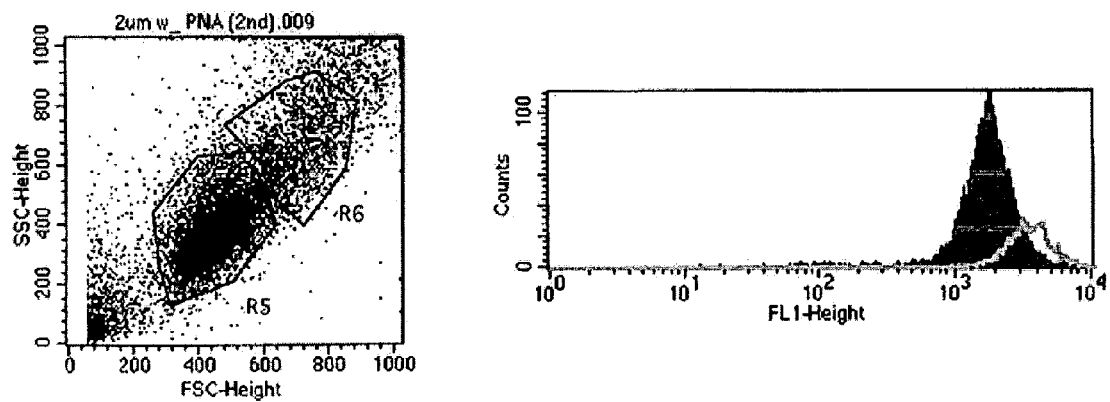

The raw data obtained by flow-FISH are shown in FIG. 6. Three types of data (front scattering signal, side scattering signal, and fluorescence signal) were obtained for each cell, and several thousand cells were analyzed in each run. The black-and-white plots on the left show the data for side scattering versus front scattering, which gives indications of groupings of cell size and granularity. The three plots show data for cells alone, for untreated cells with PNA telomere probe, and for cells treated with 2 μM circle (24 hours) then stained with the PNA probe, respectively. On the right are the fluorescence data for the same three treatments or controls. The fluorescence data are analyzed in more detail below.

Figure 7A:
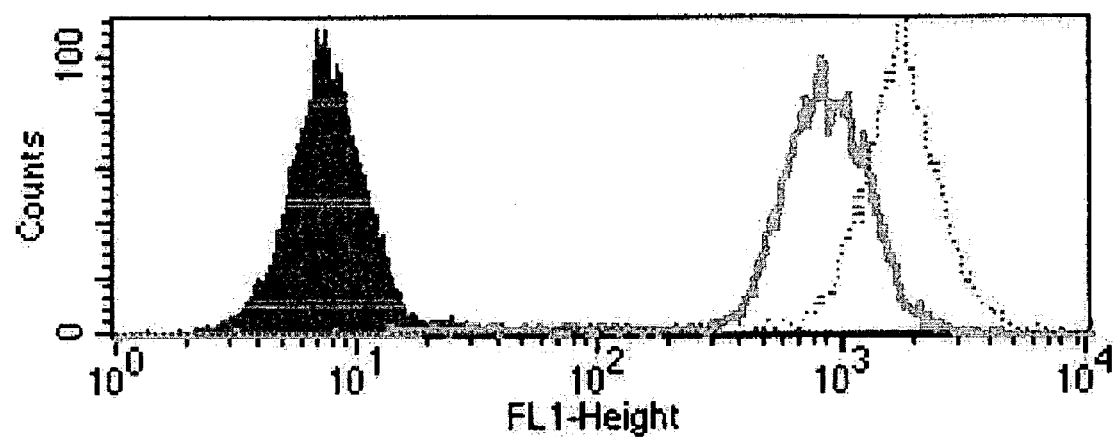
FIG. 7 shows fluorescence data for two groups of cell populations (FIGS. 7A and 7B).
Figure 7B:
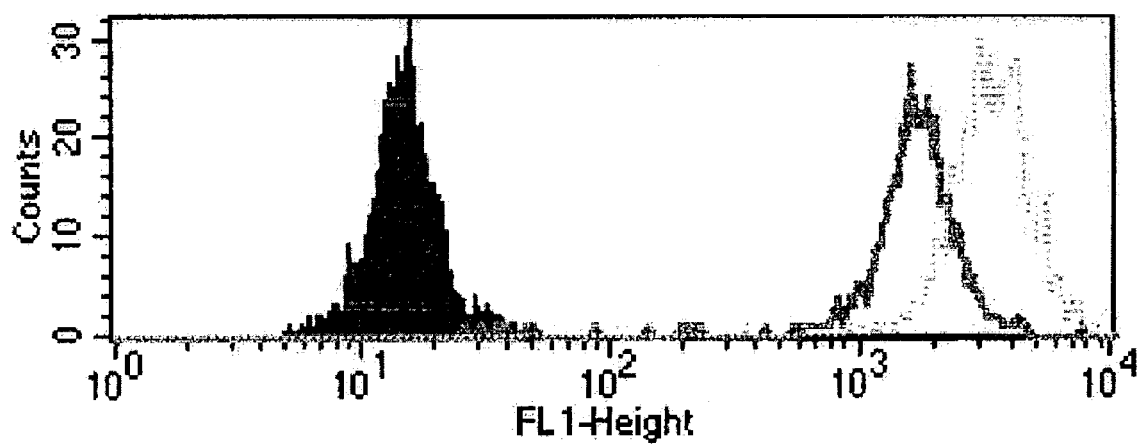

We observed two rough groupings of the cell population based on the plots of side scattering versus front scattering, so the data were analyzed for each group separately. However, both groupings of cells gave very similar results (FIG. 7).

The fluorescence data are given in two plots for the two groupings of cells. The plots show the fluorescence of untreated cells with no PNA telomere probe, untreated cells with PNA probe (showing fluorescence of untreated telomere signals), and the signals for cells treated with 2 μM circle for 24 hours, then labeled with PNA probe.

The data show that a single 24 hour treatment with HT54 circle produced significantly greater telomere signals in the flow-FISH experiment. Most telomere signals were increased, shifting virtually the entire curve of telomere signal distributions to the right. The average telomere signal was increased by a factor of greater than two. Assuming that telomere length correlates linearly with telomere probe signal, this suggests that telomere length was increased by the circle treatment by a factor of >2.

Example 24

Telomere Extension on Metaphase Chromosomes

Metaphase spreads on glass slides were prepared from human 293 human embryonic kidney cells according to standard protocols. Slides were denatured in 70% formamide/2× SSC (1×SSC=0.15 M sodium chloride/0.015 M sodium citrate, pH 7.0) for 2 minutes at 72° C. followed by dehydration in 70, 85, and 95% aqueous ethanol solutions. A 25 μl mixture containing 0.2 mM dATP, 0.2 mM dGTP, 0.02 mM dTTP, 0.05 mM fluorescein-12-dUTP (Molecular Probes), 0.5 μM HT54 nanocircle, 5 units of Taq polymerase, and Thermopol buffer (New England Biolabs) was added to one slide. A similar mixture containing no circle was added to the control slide.

Slides were incubated at 68° C. for 20 minutes followed by 1 hour at 72° C. After incubation, they were washed in 4×SSC/0.5% Tween-20 for 10 min at 65° C. followed by dehydration in 70, 85, and 95% ethanol serially. Counterstaining was performed with a 90% glycerol solution containing 4,6-diamino-2-phenylindole (0.1 μg/ml, Sigma) and diazabicyclo[2.2.2]octane (20 mg/ml, Sigma). Digital images were acquired with a SPOT charge-coupled device camera mounted on a Nikon E800 epifluorescence microscope equipped with appropriate filters. For pol β extensions, pretreatment conditions (cell preparation, denaturation, and dehydration) were identical to those for the Taq reaction. Initially, 5 μl of a 12 μM solution of HT54 circle was added to the slide and heated at 95° C. for 5 minutes. After cooling to room temperature, 10 μl of nucleotide mix (0.5 mM dATP and dGTP/50 IJ-M dTTP/130 μM fluorescein-12-dUTP) and 5 μl of polymerase solution [10 units of pol β in the buffer recommended by the manufacturer (Chimerx)] were added. The slide was sealed and incubated for 1.5 hours at 37° C. Subsequent steps (washing) were identical to those for the Taq extensions. HT54SCR (SEQ ID NO:37) was used as a scrambled circle control.

New sequences were visualized by the uptake of fluorescein-labeled dUTP in the extension reaction. Results showed that new, apparently telomeric sequences are clearly visible as green signals at chromosome ends. Controls lacking nanocircle gave no signal, and dCTP was not needed to generate this signal, consistent with the expected (TTAGGG)$_n$ (SEQ ID NO:1) sequence. Experiments with a different control, in which a circle of scrambled sequence was used (HT54SCR), showed no signals, consistent with the need for complementarity to the existing telomere end. Experiments with a second polymerase, human pol β, also showed new telomeric signals, thus establishing that (i) high temperatures are not necessary for elongation and (ii) polymerases of eukaryotic origin can function in this mechanism. The data show that the combination of a DNA polymerase and a nanocircle template effectively mimics the natural ribonucleoprotein composed of the human protein (hTERT) and the human telomerase RNA template. This approach offers and efficient and simple method for the production of long telomeric repeats, and may have utility in the study of the unusual secondary and tertiary structures formed by telomeres and their associated proteins. Chimeric nanocircles can be used to encode chimeric telomeres which are not possible to prepare by altering the human telomerase RNA template sequence.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. An isolated nucleic acid nanocircle consisting of an integral number of a telomere repeat sequence, wherein the length of the nanocircle is 30 nucleotides, 36 nucleotides, 42 nucleotides, 48 nucleotides, 54 nucleotides, 60 nucleotides, 66 nucleotides, 72 nucleotides, or 78 nucleotides.

2. The nanocircle of claim 1, wherein the telomere repeat sequence is 5'-CCCTAA-3' (SEQ ID NO:3), 5'-CCCUAA-3' (SEQ ID NO:4), 5'-TTAGGG-3' (SEQ ID NO:63), or 5'-UUAGGG-3' (SEQ ID NO:64).

3. The nanocircle of claim 1, wherein the nanocircle is HT30(SEQ ID NO:26), HT36 (SEQ ID NO:27), HT42 (SEQ ID NO:28), HT48 (SEQ ID NO:29), HT54 (SEQ ID NO:30), HT60(SEQ ID NO:31), HT66 (SEQ ID NO:32), HT72 (SEQ ID NO:33), or HT78 (SEQ ID NO:34).

4. The nanocircle of claim 1, wherein the nanocircle is a DNA nanocircle.

5. The nanocircle of claim 1, wherein the nanocircle is a RNA nanocircle.

6. The nanocircle of claim 1, wherein the nanocircle is single stranded.

7. The nanocircle of claim 1, wherein the nanocirele is double stranded.

* * * * *

UNITED STATES PATENT AND TRADEMARK OFFICE
CERTIFICATE OF CORRECTION

| | | |
|---|---|---|
| PATENT NO. | : 7,482,332 B2 | Page 1 of 1 |
| APPLICATION NO. | : 10/336265 | |
| DATED | : January 27, 2009 | |
| INVENTOR(S) | : Kool | |

It is certified that error appears in the above-identified patent and that said Letters Patent is hereby corrected as shown below:

In The Specification Under Column 1:

• Please replace lines 15-17 with:

-- This invention was made with Government support under contract DAMD17-98-1-8239 awarded by the Department of the Army/MRMC. The Government has certain rights in this invention. --

Signed and Sealed this
Nineteenth Day of April, 2011

David J. Kappos
*Director of the United States Patent and Trademark Office*